United States Patent
Tsim et al.

(10) Patent No.: US 9,217,733 B2
(45) Date of Patent: Dec. 22, 2015

(54) METHOD AND SYSTEM FOR DETECTING RESIDUAL POISON IN HUMAN BODY

(75) Inventors: Karl Wah Keung Tsim, Hong Kong (HK); Tina Tingxia Dong, Hong Kong (HK); Kevin Yue Zhu, Hong Kong (HK); Ka Wing Leung, Hong Kong (HK); Tiejie Wang, Shenzhen (CN)

(73) Assignee: The Hong Kong University of Science and Technology, Hong Kong (HK)

( * ) Notice: Subject to any disclaimer, the term of this patent is extended or adjusted under 35 U.S.C. 154(b) by 468 days.

(21) Appl. No.: 13/508,043

(22) PCT Filed: Nov. 5, 2010

(86) PCT No.: PCT/CN2010/078468
§ 371 (c)(1),
(2), (4) Date: May 4, 2012

(87) PCT Pub. No.: WO2011/054313
PCT Pub. Date: May 12, 2011

(65) Prior Publication Data
US 2012/0220039 A1 Aug. 30, 2012

(30) Foreign Application Priority Data
Nov. 5, 2009 (CN) .......................... 2009 1 0221092

(51) Int. Cl.
*G01N 33/00* (2006.01)
*G01N 30/72* (2006.01)
*G01N 30/34* (2006.01)
*G01N 33/94* (2006.01)
(Continued)

(52) U.S. Cl.
CPC ............ *G01N 30/7233* (2013.01); *G01N 30/34* (2013.01); *G01N 33/94* (2013.01); *G01N 33/4833* (2013.01); *H01J 49/00* (2013.01); *Y10T 436/141111* (2015.01); *Y10T 436/142222* (2015.01); *Y10T 436/145555* (2015.01); *Y10T 436/173845* (2015.01); *Y10T 436/174614* (2015.01)

(58) Field of Classification Search
None
See application file for complete search history.

(56) References Cited

U.S. PATENT DOCUMENTS 5,142,144 A    8/1992  Remo et al.
2006/0193748 A1 *  8/2006  Tai et al. ..................... 422/70

FOREIGN PATENT DOCUMENTS

CN         1609610 A    4/2005
CN       101750458 A    6/2010
(Continued)

OTHER PUBLICATIONS

Valaskovic, G. A. et al. Automated Orthogonal Control System for Electrospray Ionization, 2004, Journal of American Society for Mass Spectrometry, vol. 15, pp. 1201-1215.*
(Continued)

*Primary Examiner* — Robert Xu
(74) *Attorney, Agent, or Firm* — Ella Cheong Hong Kong; Sam T. Yip

(57) ABSTRACT

A method and system for detecting residual poison in human body are provided. Using the disclosed HPLC-Chip-mass spectrometry (MS)/MS and/or HPLC-MS/MS method to detect the residual poison, the method of the present invention mainly includes sample preparation, liquid chromatography and mass spectrometry. The method of the present invention has advantages of low sample size, high specificity, low detection limit, high sensitivity, low cost, high accuracy and stability, etc.

15 Claims, 30 Drawing Sheets

(51) Int. Cl.
*G01N 33/483* (2006.01)
*H01J 49/00* (2006.01)

(56) References Cited

FOREIGN PATENT DOCUMENTS

EP          0229517 A1    7/1987
WO    WO 2007/089923  *   8/2007  ............. A61K 38/16

OTHER PUBLICATIONS

Sooyeun Lee, Jihyun Kim, Sanghwan In, Hwakyung Choi, Seung Min Oh, Choon-Gon Jang, Kyu Hyuck Chung, Development of a simultaneous analytical method for selected anoretics, methamphetamine, MDMA, and their metabolites in hair using LC-MS/MS to prove anorectics abuse. Mar. 30, 2012, pp. 110, Springer, Korea.

Aldo Polettini, Edwar J. Cone, David A. Gorelick, Marilyn A. Huestis, Incorporation of methamphetamine and amphetamine in human hair following controlled oral methamphetamine administration. Analytica Chimica Acta 726, Jan. 2012, pp. 35-43, Elsevier B.V, USA.

E. Gallardo, M. Barroso, J.A. Queiroz, LC-MS a powerful tool in workplace drug testing, Drug Test.Analysis, 2009, pp. 109-115, John Wiley & Sons.

Tabernero MJ et al., Determination of ketamine and amphetamines in hair by LC/MS/MS, Anal Bioanal Chem, 2009, vol. 395, pp. 2547-2557, Springer.

Xiang Ping et al., "Analysis of Ketamine in Hair", Journal of Forensic Medicine, 2005, vol. 21, No. 4, p. 290-293.

Zhang Yueqin et al., "Progress in A745nalysis Method of Ketamine and Metabolites in Biological Samples", Chemistry Online, 2008, vol. 10, p. 739-745.

Chen Hua et al., "Determination of Cannabis in Human Hair", Chinese Pharmaceutical Affairs, 2009, vol. 23, No. 8, p. 810-812.

Office Action of CN 201080049909.6 issued from the State Intellectual Property Office of the People's Republic of China on Jun. 9, 2014.

* cited by examiner

METHOD AND SYSTEM FOR DETECTING RESIDUAL POISON IN HUMAN BODY

CROSS-REFERENCE TO RELATED APPLICATIONS

The present application is a national phase application of the international patent application number PCT/CN2010/078468 filed Nov. 5, 2010 which claims priority from a Chinese invention patent application number 200910221092.5 filed Nov. 5, 2009, and the disclosure of which is incorporated herein by reference and its entirety.

TECHNICAL FIELD

The present invention belongs to the area of biomedical detection technology. In particular, the present invention describes a rapid method and its associated detection system for detecting drug residues in human body.

BACKGROUND OF THE INVENTION

Recent surveys showed an increasing trend of drug abuse, especially in teenager groups of Hong Kong and Shenzhen, and it seems to be spiraling out of control. Drug detection tests would be an important part of the drug control scheme. Blood test and urine test are the common methods in recent decades. The prominent disadvantages include collection complexity, dilution effects, faked sampling problems and short detection periods (less than 7 days).

Meanwhile, using hair specimens in abused drug detection would be preferred as supplemental evidence for determination of drug use. The first advantage of using hair as a specimen is that it could show the drug-taking history up to 1 year if the hair is longer than 12 cm. Second, embarrassment is avoided during collection of hair samples. It is therefore believed that hair drug tests would be a good alternative to using urine samples.

Ketamine ("K" as street name) is currently used as veterinary and human anesthetic. Ketamine is classified as an NMDA receptor antagonist. When ketamine is used as a recreational drug, it induces a "dissociative" status of the abuser (mind "separates" from the body). Ketamine abusers are often unconscious and unable to respond to physical stimulation. Furthermore, ketamine has damaging effects cardiovascular, respiratory and nervous systems.

Methadone is an artificial opiate derivate which has been used for the treatment of dependency of opiates such as heroin and morphine. Clinically, methadone is used to relieve severe chronic pain due to its long lasting action. Methadone is associated with respiratory depression, decreases in heart rate and blood pressure. Individuals who abuse methadone become tolerant and physically depend on methadone during withdrawal treatment.

Opiates include mono-acetylmorphine, morphine, codeine and heroin. Morphine is the abundant alkaloid found in opium and is a potent opiate analgesic compound to relieve severe pain. Morphine abuser can rapidly develop addiction, tolerance and psychological dependence.

Heroin (diacetylmorphine) is morphine alkaloid. Its street name is called "white powder". Heroin is produced from acetylation of morphine. It is typically used as an analgesic drug to treat severe pain. Long term administration causes tolerance, physical dependence and hence addiction. Drug use by injection could cause risk in spreading of blood-borne disease such as AIDS. Heroin is rapidly metabolized into 6-monoacetylmorphine and morphine once administered. 6-monoacetylmorphine is targeted to monitor for abuse.

Cocaine is a powerful stimulant of the central nervous system and a topical anesthetic. Cocaine increases alertness, euphoria, energy and motor activity. Regular use of cocaine results to psychological dependence and addiction. Because cocaine is usually metabolized into the major metabolite benzoylecgonine (BE), BE is also included in the drug test of cocaine.

Amphetamines includes amphetamine, methamphetamine, MDMA and MDA. Amphetamine is a psycho-stimulant and produce wakefulness and medically used in the association with fatigue. Amphetamine has been limited to prescription use by FDA. The side effects of amphetamine use are mental fatigue, mental depression.

Methamphetamine is a psycho-stimulant of the amphetamine class of psychoactive drugs. Its street name often called "ice" or "speed" because of its crystal appearance. Methamphetamine has high potential for abuse and addiction. Its effects include hyperactivity, hallucinations and reduction in appetite. Long term use of methamphetamine associates with depression, suicide, violent behaviors and psychosis.

MDMA (3,4-methylenedioxy-N-methylamphetamine) belongs to amphetamine class of drug. It is widely known as "ecstasy". The psychoactive properties of MDMA induce euphoria, increased energy, hyperactive, increased motivation, sexual assault and violent behaviors. MDMA will be metabolized into MDA (3,4-methylenedioxyamphetamine). MDMA and MDA are often quantified in the drug test in blood and urine.

SUMMARY OF THE INVENTION

The first aspect of the present invention relates to a method for detecting drug residues in human hair, urine, seat and oral secretion by incorporating a novel hair sampling scheme and High Performance Liquid Chromatography-Chip-Mass Spectrometry (HPLC-Chip-MS/MS) technology with high sensitivity and reliability. The method of the present invention mainly includes: (1) Sample preparation; (2) Liquid Chromatography; and (3) Mass Spectrometry. Specific conditions of (2) liquid chromatography may include:
  i. Capillary pump having the following conditions: Mobile phase A (0.1-0.2% formic acid in water); Mobile phase B (0.1-0.2% formic acid in acetonitrile); Flow rate: 1-6 μL/min; Mobile phase A gradient (10-97%); Mobile phase B gradient (90-3%); or
  ii. Nano pump having the following conditions: Mobile phase A and B are the same to that of the capillary pump; Flow rate: 0.1-0.6 μL/min; Mobile phase A gradient (5-97%); Mobile phase B gradient (95-3%); and
  iii. Chip injection volume: 2-4 μL.

Specific conditions of (3) mass spectrometry (MS) may include: Drying gas temperature: 325° C.; Drying gas flow: 4 L/min; Capillary voltage: 1950V; Polarity: Positive ion mode; Scan mode: Multiple Reaction Monitoring (MRM); Ion pair detection: two parent-product ions detection (parameters are referred to respective target drugs).

The target drugs that the method of the present invention is capable of detecting include ketamine, methadone, morphine, 6-acetylmorphine (metabolite of heroin), cocaine, benzoylecgonine (metabolite of cocaine), amphetamine, methamphetamine, MDMA and MDA. The ion pair used in the method of the present invention for each of these drugs includes:
  i. Ketamine: 238.1>128.0, 238.1>89.0
  ii. Methadone: 310.2>265.1, 310.2>91.0 iii. Morphine: 286.1>128.1, 286.1>115.0
iv. 6-acetylmorphine (metabolite of heroin): 328.0>165.0, 328.0>211.0
v. Cocaine: 304.2>105.0, 304.2>182.1
vi. Benzoylecgonine (metabolite of cocaine): 290.1>168.0, 290.1>105
vii. Amphetamine: 136.1>91.0, 136.1>119.0
viii. Methamphetamine: 150.1>65.0, 150.1>91.0
ix. MDMA: 194.1>163.0, 194.1>105
x. MDA: 180.1>135.0, 180.1>163.0

The second aspect of the present invention relates to a method for detecting drug residues in human hair, urine, sweat and oral secretion by incorporating a novel hair sampling scheme and High Performance Liquid Chromatography-Mass Spectrometry (HPLC-MS/MS) technology. The method of the present invention mainly includes: (1) Sample preparation; (2) Liquid chromatography; and (3) Mass spectrometry. Specific conditions of (2) liquid chromatography may include:
(i) Capillary pump conditions: Mobile phase A (0.1-0.2% formic acid in water); Mobile phase B (0.1-0.2% formic acid in acetonitrile); Flow rate: 0.1-0.6 mL/min; Mobile phase A gradient (10-97%); Mobile phase B gradient (90-3%). Specific conditions of (3) mass spectrometry (MS) may include: Drying gas temperature: 325° C.; Drying gas flow: 10 L/min; Capillary voltage: 4000V; Polarity: Positive ion mode; Scan mode: Multiple Reaction Monitoring (MRM); Ion pair detection: two parent-product ions detection (parameters are referred to respective target drugs).

The target drugs that the method of the present invention is capable of detecting include ketamine, methadone, morphine, 6-acetylmorphine (metabolite of heroin), cocaine, benzoylecgonine (metabolite of cocaine), amphetamine, methamphetamine, MDMA and MDA. The ion pair used in the method of the present invention for some of these drugs includes:
i. Ketamine: 238.1>125.0, 238.1>89.0;
ii. Methadone: 310.2>265.1, 310.2>91.0;
iii. Amphetamine: 136.1>91.0, 136.1>119.0;
iv. Methamphetamine: 150.1>65.0, 150.1>119.0

The human hair that the methods of the present invention are capable of detecting the drug residues therein include head hair, armpit hair, pubic hair and beard hair.

In an embodiment of detecting the drug residues in human hair, the (1) sample preparation of the methods of the present invention includes:
i. Collecting the human hair at different lengths;
ii. Washing the collected hair sample in 0.2% SDS, deionized water and acetone by ultrasonication;
iii. Drying by nitrogen gas, 0.5 mL hydrochloric acid (0.15 mol/L) is added for digestion for 4 hours at 60° C. water bath;
iv. Cooling to room temperature, 0.03 mL sodium hydroxide (2 mol/L) and 2 mL sodium phosphate buffer (0.1 mol/L, pH 6.8) are added for neutralization;
v. 2 mL of extraction mixture (90:10 v/v, dichloromethane: hexane) is added for phase extraction by vortexing for 5 minutes;
vi. The sample is taken for centrifugation;
vii. The lower organic phase is collected and dried by nitrogen gas;
viii. The sample is resuspended with 50 μL of acetonitrile;
ix. 5 μL of the resuspended sample is used for liquid chromatography.

The present invention incorporates HPLC-CHIP-MS/MS and HPLC-MS/MS technology in the detection of drug residues. (HPLC-CHIP-MS/MS method was adopted for the detection of commonly abused drugs, viz cocaine, heroin, MDMA/Ecstasy, amphetamine, morphine, ketamine, methadone and methamphetamine. A system according to the HPLC-CHIP-MS/MS method of the present invention is also disclosed in the present invention, which mainly adopts a microfluidic chip-based technology to create a nanospray LC/MS. HPLC-Chip technology is also adopted in the system of the present invention to achieve sample analysis at a very low concentration. Such technology provides higher sensitivity, chromatographic performance, reproducibility, and stability than the traditional HPLC or GC (gas chromatography). The HPLC-Chip in the system of the present invention has a close-channel design to reduce connections, leakage and dead-volume. The advantages of this design include an enhanced sensitivity, a decrease in sample amount and the time for analysis. The detection sensitivity of the system of the present invention can be up to pico-gram level (pg), which is suitable for detecting a trace amount of drugs in a hair sample for as long as 90 days. Accordingly, the number of hair strands collected for detection of drug residues is significantly reduced to only few strands of hair for analysis. The methods are more sensitive than the existing ones, and also give a lower testing cost on average and much shorter testing time.

DETAILED DESCRIPTION OF THE INVENTION

Figure 1A:
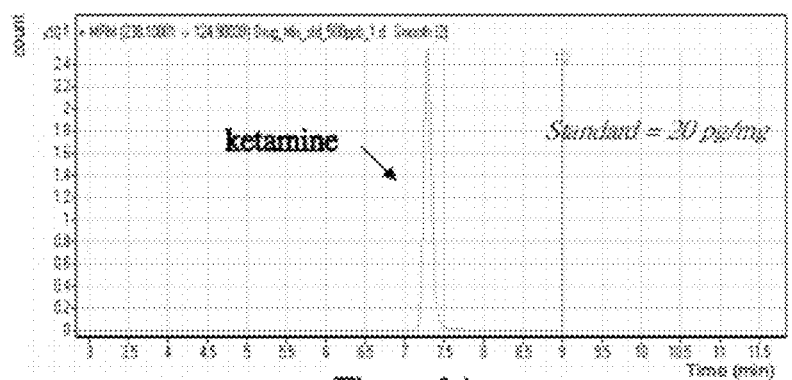
FIG. 1: HPLC-Chip-MS/MS ketamine MRM spectrum. (A) MRM spectrum from blank hair sample spiked with ketamine standard (20 pg/mg). (B) Calibration curve from blank hair sample spiked with ketamine standard. (C). MRM spectrum from blank hair sample spiked with ketamine standard at the limit of quantification (LOQ) (1 pg/mg). (D) MRM spectrum from blank hair sample spiked with ketamine standard at the limit of detection (LOD) (0.1 pg/mg).
Figure 1B:
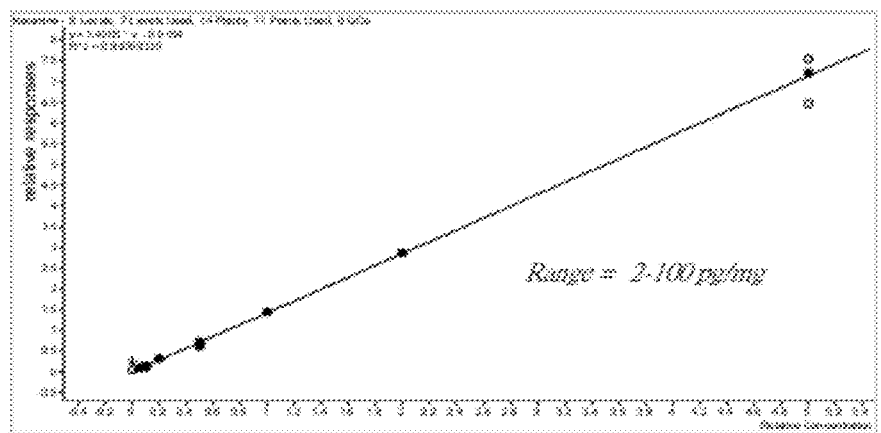
Figure 1C:
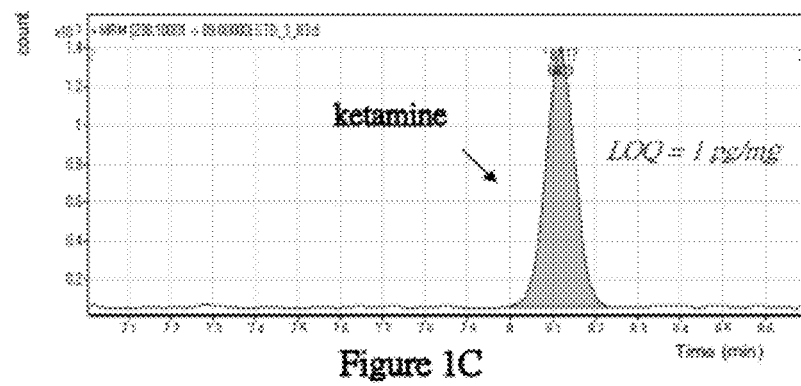
Figure 1D:
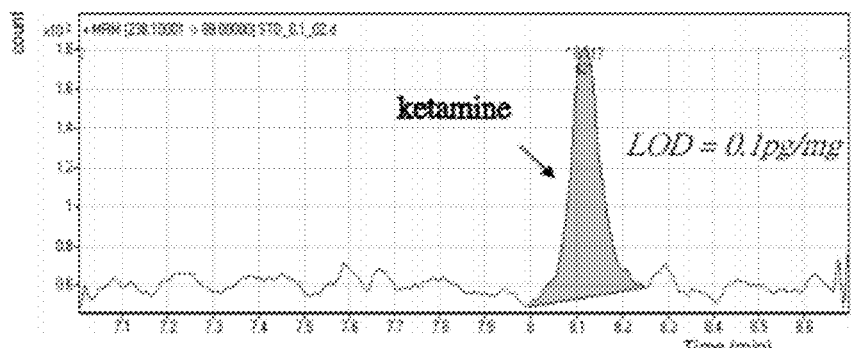
Figure 2A:
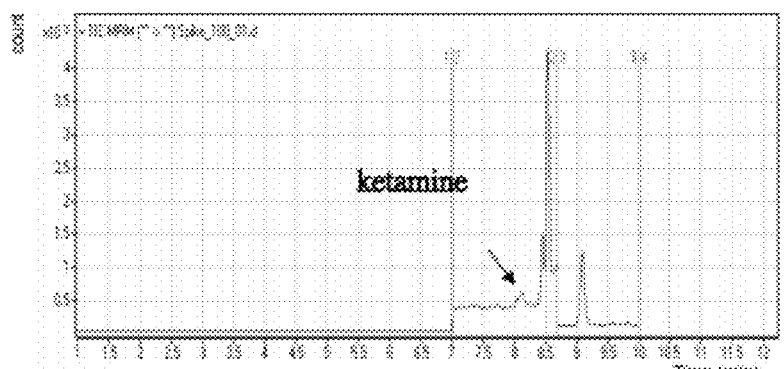
FIG. 2: HPLC-Chip-MS/MS analysis in hair of ketamine user. (A) Total ion count chromatogram of ketamine user hair sample. (B) MRM chromatogram of ketamine user hair sample. (C) Product ion MRM chromatogram of ketamine user hair sample.
Figure 2B:
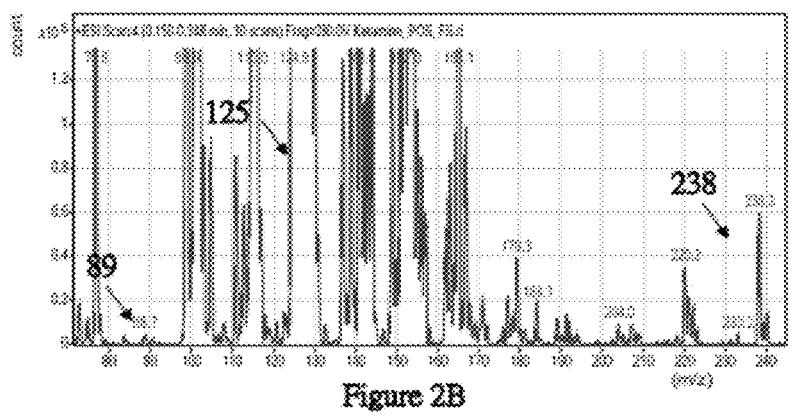
Figure 2C:
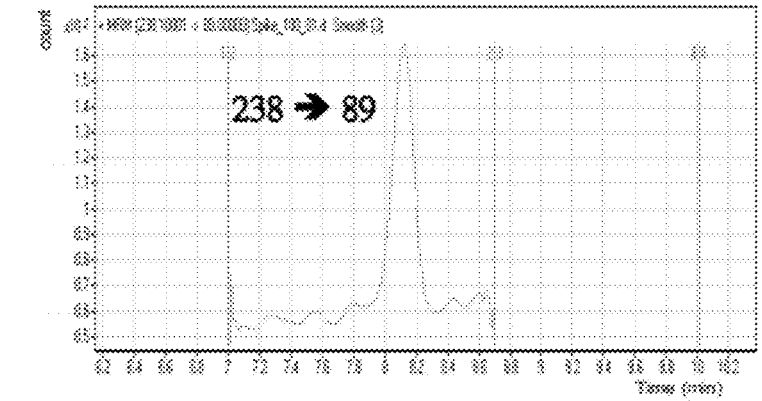
Figure 2C:
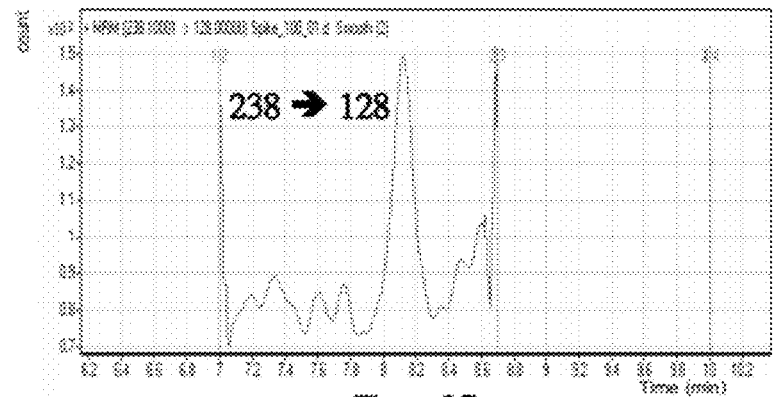
Figure 3A:
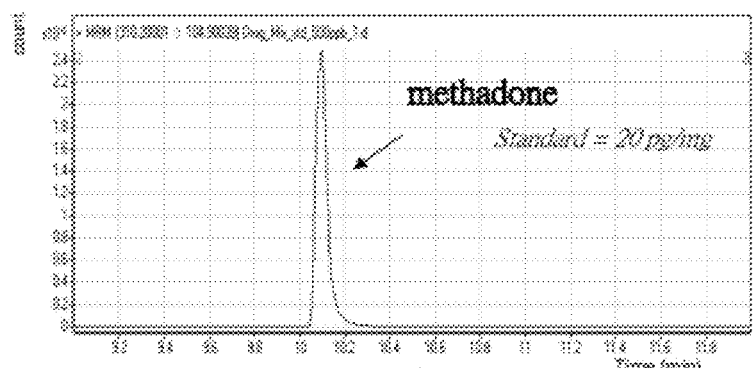
FIG. 3: HPLC-Chip-MS/MS methadone MRM spectrum. (A) MRM spectrum from blank hair sample spiked with methadone standard (20 pg/mg). (B) Calibration curve from blank hair sample spiked with methadone standard. (C). MRM spectrum from blank hair sample spiked with methadone standard at the limit of quantification (LOQ) (0.5 pg/mg). (D) MRM spectrum from blank hair sample spiked with methadone standard at the limit of detection (LOD) (0.1 pg/mg).
Figure 3B:
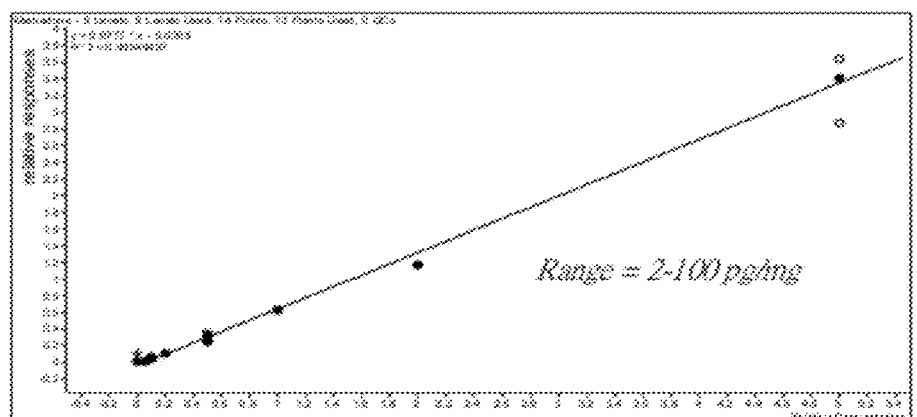
Figure 3C:
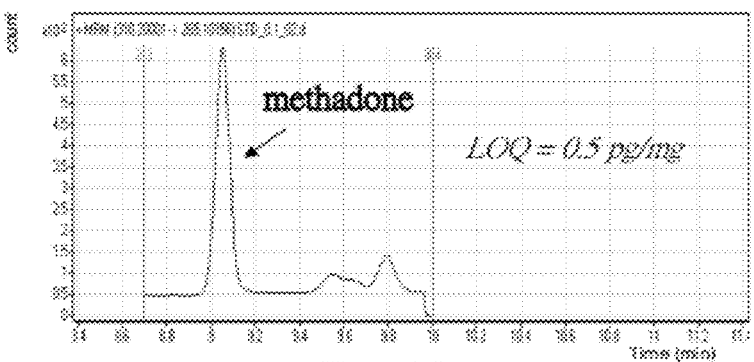
Figure 3D:
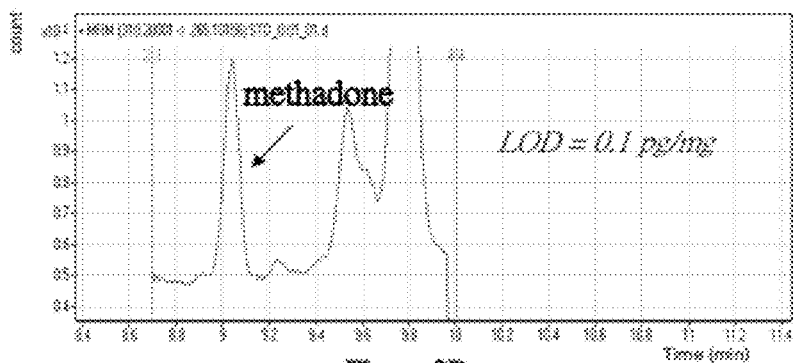
Figure 4A:
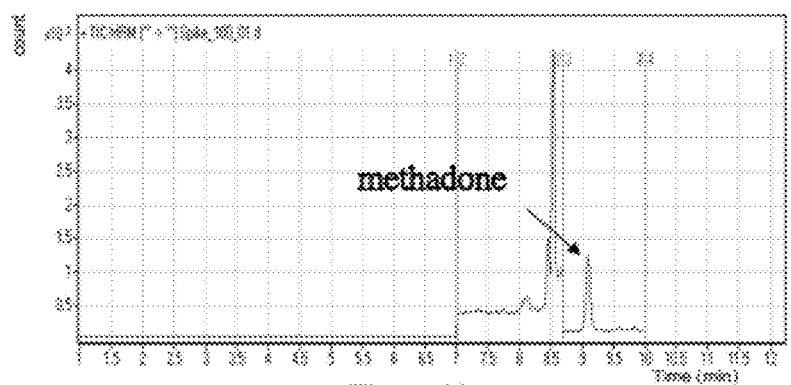
FIG. 4: HPLC-Chip-MS/MS analysis in hair of methadone user. (A) Total ion count chromatogram of methadone user hair sample. (B) MRM chromatogram of methadone user hair sample. (C) Product ion MRM chromatogram of methadone user hair sample.
Figure 4B:
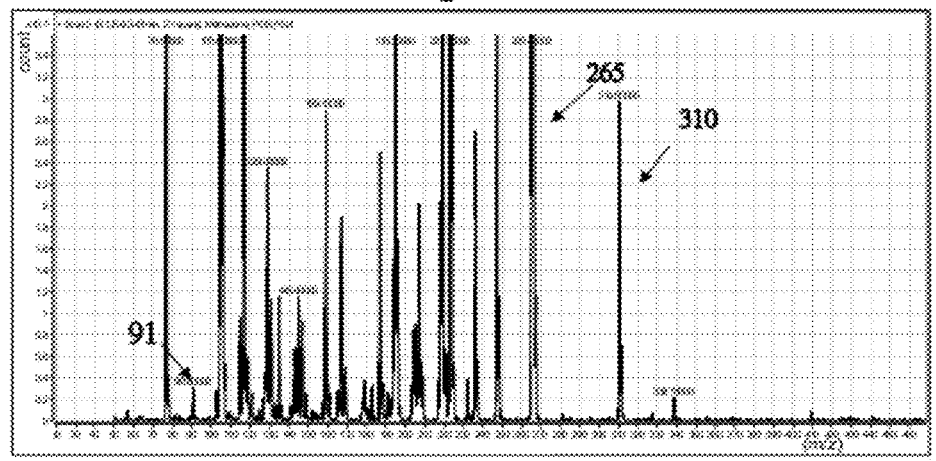
Figure 4C:
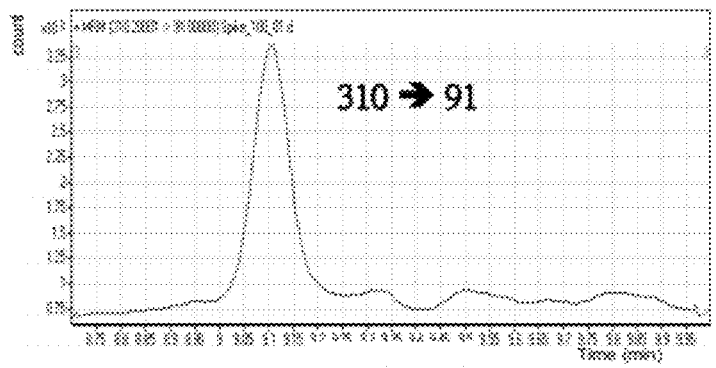
Figure 4C:
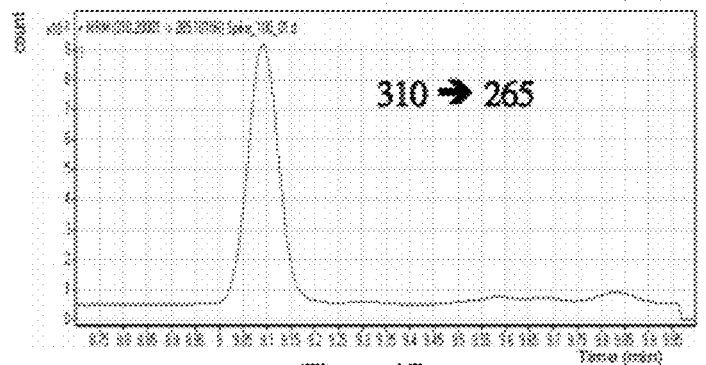
Figure 5A:
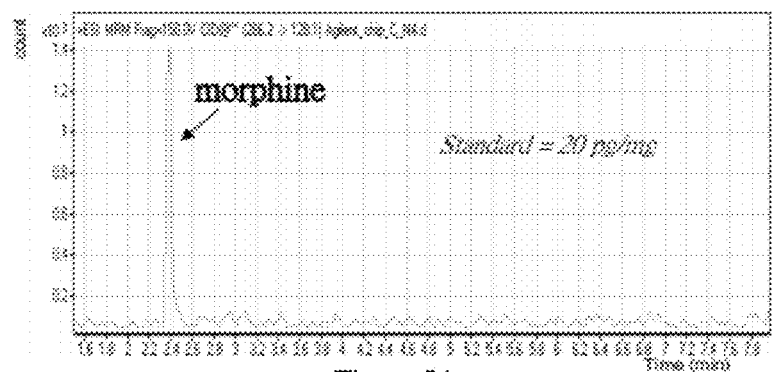
FIG. 5: HPLC-Chip-MS/MS morphine MRM spectrum. (A) MRM spectrum from blank hair sample spiked with morphine standard (20 pg/mg). (B) Calibration curve from blank hair sample spiked with morphine standard. (C) MRM spectrum from blank hair sample spiked with morphine standard at the limit of quantification (LOQ) (10 pg/mg). (D) MRM spectrum from blank hair sample spiked with morphine standard at the limit of detection (LOD) (2 pg/mg).
Figure 5B:
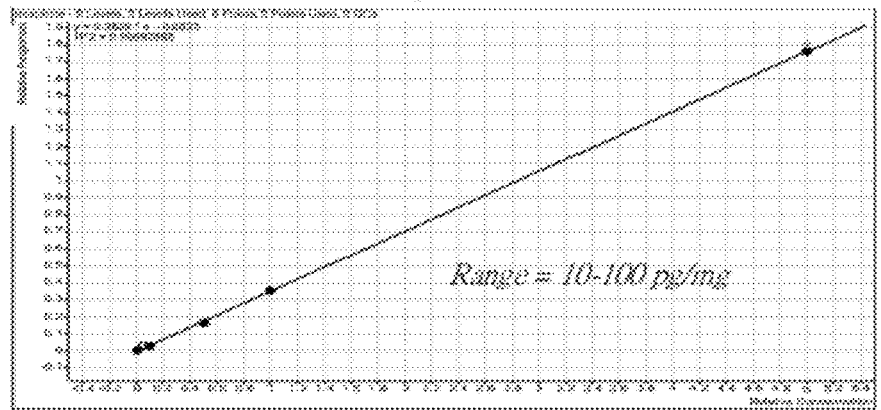
Figure 5C:
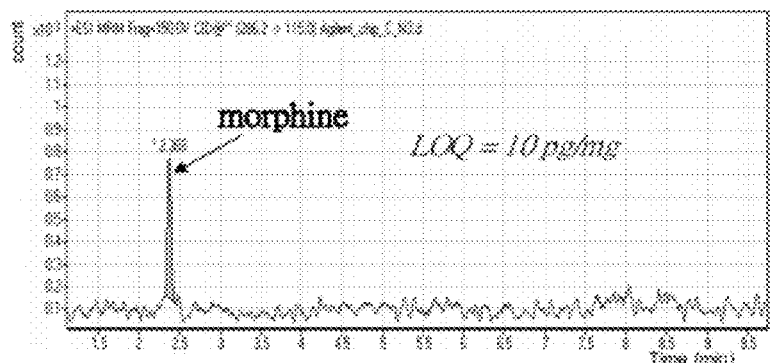
Figure 5D:
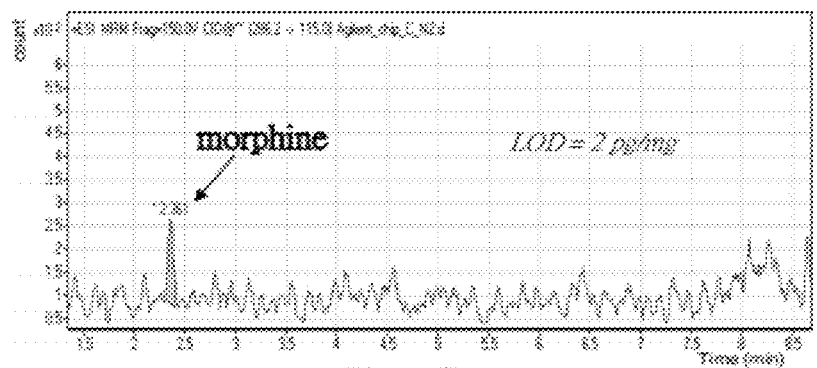
Figure 6A:
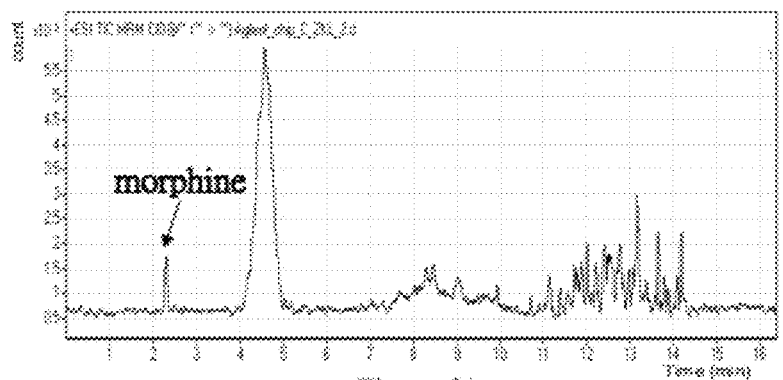
FIG. 6: HPLC-Chip-MS/MS analysis in hair of morphine user. (A) Total ion count chromatogram of morphine user hair sample. (B) MRM chromatogram of morphine user hair sample. (C) Product ion MRM chromatogram of morphine user hair sample.
Figure 6B:
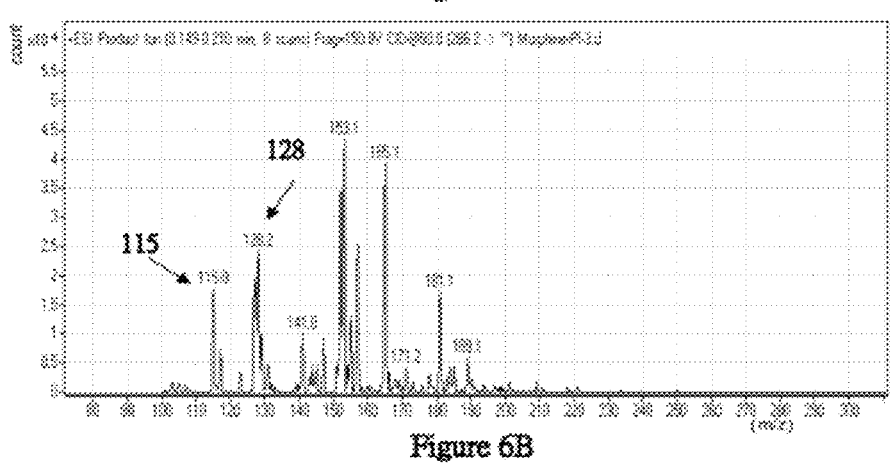
Figure 6C:
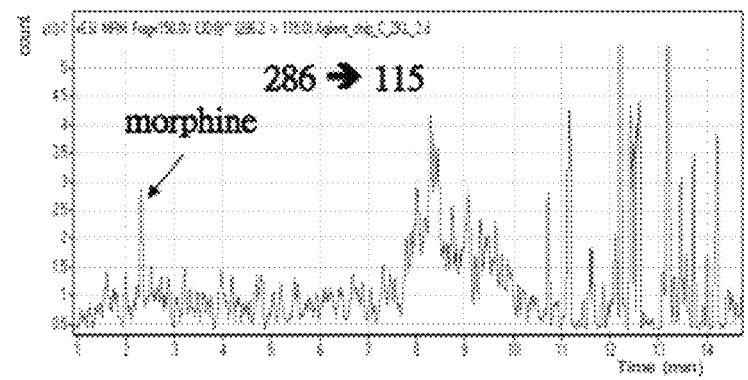
Figure 6C:
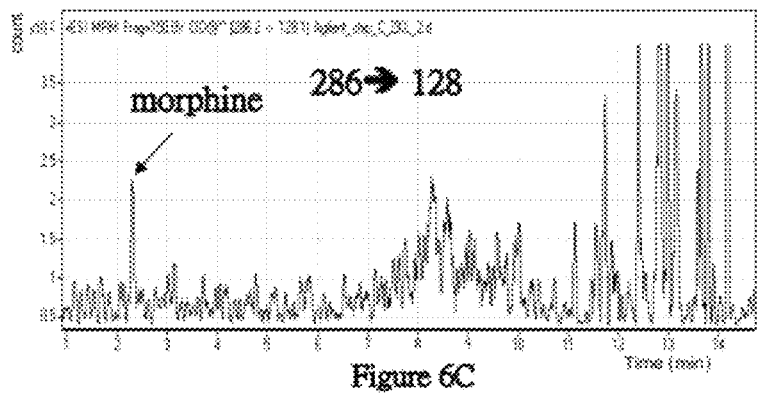
Figure 7A:
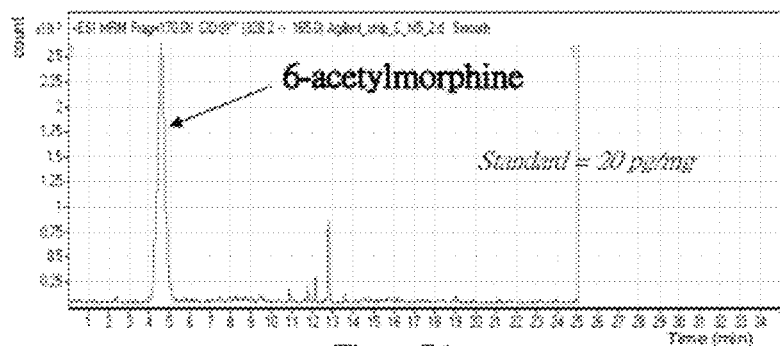
FIG. 7: HPLC-Chip-MS/MS 6-acetylmorphine MRM spectrum. (A) MRM spectrum from blank hair sample spiked with 6-acetylmorphine standard (20 pg/mg). (B) Calibration curve from blank hair sample spiked with 6-acetylmorphine standard. (C) MRM spectrum from blank hair sample spiked with 6-acetylmorphine standard at the limit of quantification (LOQ) (10 pg/mg). (D) MRM spectrum from blank hair sample spiked with 6-acetylmorphine standard at the limit of detection (LOD) (2 pg/mg).
Figure 7B:
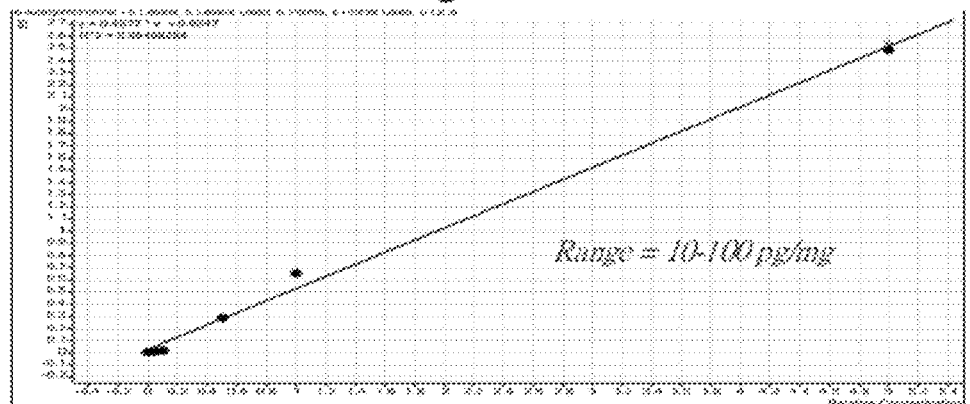
Figure 7C:
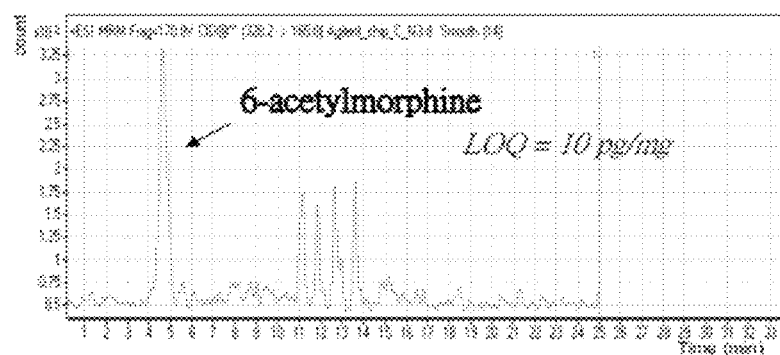
Figure 7D:
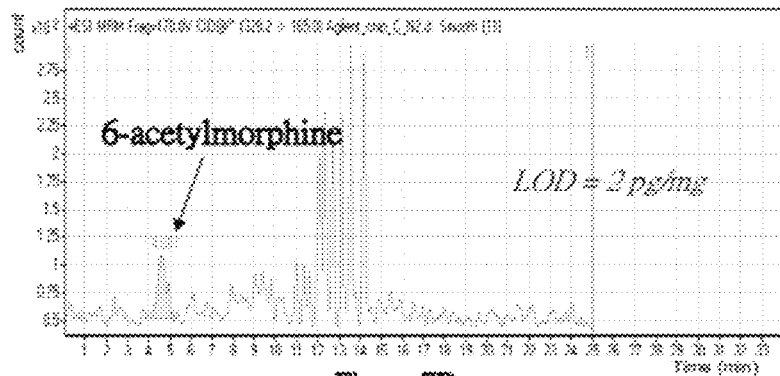

The practical examples using the methods of the present invention are described as below:

Example 1

Use of HPLC-Chip-MS/MS Method in Ketamine Detection

The procedures for the detection of ketamine in human hair by the HPLC-Chip-MS/MS method of the present invention are as follows:
(1) Sample Preparation
1. Hair was washed in 0.2% SDS, deionized water and acetone by ultrasonication. After drying by nitrogen gas, 0.5 mL hydrochloric acid (0.15 mol/L) was added for digestion for 4 hours at 60° C. water bath.
2. After cooling to room temperature, 0.03 mL sodium hydroxide (2 mol/L) and 2 mL sodium phosphate buffer (0.1 mol/L, pH 6.8) were added for neutralization.
3. 2 mL of extraction mixture (90:10 v/v, dichloromethane:hexane) was added for phase extraction by vortexing for 5 minutes. Then, the sample was taken for centrifugation.
4. The lower organic phase was collected and dried by nitrogen gas. Then, sample was resuspended with 50 µL of acetonitrile. 5 µL was used for liquid chromatography.
(2) Liquid Chromatography Conditions:
1. Instruments:
Agilent 1200 Series LC (Agilent Technologies, Waldbronn, Germany); Analytical column: Agilent chip Zorbax 80SB-C18, 5 µm (Separation: 150 mm×75 µm, Enrichment: 25 mm, 500 nl); Chip is directly installed on the ion source with a micro-camera for monitoring of ionization spray. Chip cube includes chip holder for loading and ejecting chip, valve stator for solvent switching, linkage to micro-plate autosampler with capillary tube and nano electro-ionization spray for ionization. Data acquisition and analysis are performed by Mass Hunter ChemStation Softeare (version B01.03).
2. Capillary Pump Conditions:
Mobile phase A (0.1% formic acid in water); Mobile phase B (0.1% formic acid in acetonitrile); Injection volume: 2 µL; Flow rate: 1-6 µL/min (4 µL/min is preferred); Gradient: 0 min (3% B), 3 min (90% B), 5 min (90% B), 5.1 min (3% B), 25 min (3% B).
3. Nano Pump Conditions:
Mobile phase A (0.1% formic acid in water); Mobile phase B (0.1% formic acid in acetonitrile); Flow rate: 0.1-0.6 µL/min (0.4 µL/min is preferred); Gradient: 0 min (3% B), 3 min (3% B), 5 min (95% B), 12 min (95% B), 12.1 min (3% B), 25 min (3% B).
4. Chip Cube Conditions: Injection Flushing Volume (4 µL)
(3) Mass Spectrometry (MS) Conditions:
Instruments: Agilent QQQ 6410A
Drying gas temperature: 325° C.
Drying gas flow: 4 L/min
Capillary voltage: 1950V
Polarity: Positive ion mode
Scan mode: Multiple Reaction Monitoring (MRM)
Product ion detection: 238.1>128.0, 238.1>89.0

The detection of ketamine by the HPLC-Chip-MS/MS method is illustrated in FIGS. 1 and 2. FIG. 1 showed the MRM spectrum from blank hair sample spiked with ketamine standard, the calibration curve from blank hair sample spiked with ketamine standard, the limit of quantification (LOQ) and the limit of detection (LOD). FIG. 2 showed the chromatograms of hair analysis of ketamine by the method of the present invention. The presence of ketamine in the hair sample was shown by the presence of ketamine chromatographic peaks.

Example 2

Use of HPLC-Chip-MS/MS Method in Methadone Detection

Same sample preparation, liquid chromatography conditions and mass spectrometry (MS) conditions as Example 1 are used in this example (except product ion detection). The product ion detection used in this example is 310.2>265.1, 310.2>91.0

The detection of methadone by the HPLC-Chip-MS/MS method is illustrated in FIGS. 3 and 4. FIG. 3 showed the MRM spectrum from blank hair sample spiked with methadone standard, the calibration curve from blank hair sample spiked with methadone standard, the limit of quantification (LOQ) and the limit of detection (LOD). FIG. 4 showed the chromatograms of hair analysis of methadone by the method of the present invention. The presence of methadone in the hair sample was shown by the presence of methadone chromatographic peaks.

Example 3

Use of HPLC-Chip-MS/MS Method in Morphine Detection

Same sample preparation, liquid chromatography conditions and mass spectrometry (MS) conditions as Example 1 are used in this example (except injection flushing volume and product ion detection). The injection flushing volume used in this example is 2 µL; the product ion detection used in this example is 286.1>128.1, 286.1>115.0

The detection of morphine by the HPLC-Chip-MS/MS method is illustrated in FIGS. 5 and 6. FIG. 5 showed the MRM spectrum from blank hair sample spiked with morphine standard, the calibration curve from blank hair sample spiked with morphine standard, the limit of quantification (LOQ) and the limit of detection (LOD). FIG. 6 showed the chromatograms of hair analysis of morphine by the method of the present invention. The presence of morphine in the hair sample was shown by the presence of morphine chromatographic peaks.

Example 4

Use of HPLC-Chip-MS/MS Method in 6-Acetylmorphine Detection

Same sample preparation, liquid chromatography conditions and mass spectrometry (MS) conditions as Example 1 are used in this example (except injection flushing volume and product ion detection). The injection flushing volume used in this example is 2 μL; the product ion detection is 328.0>165.0, 328.0>211.0

Figure 8A:
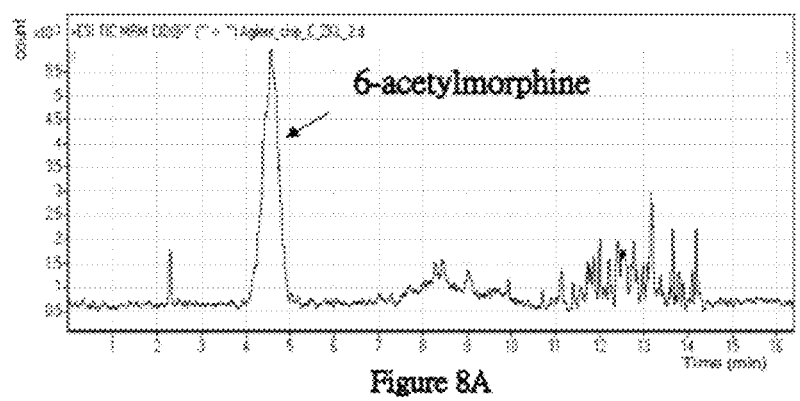
FIG. 8: HPLC-Chip-MS/MS analysis in hair of 6-acetylmorphine user. (A) Total ion count chromatogram of 6-acetylmorphine user hair sample. (B) MRM chromatogram of 6-acetylmorphine user hair sample. (C) Product ion MRM chromatogram of 6-acetylmorphine user hair sample.
Figure 8B:
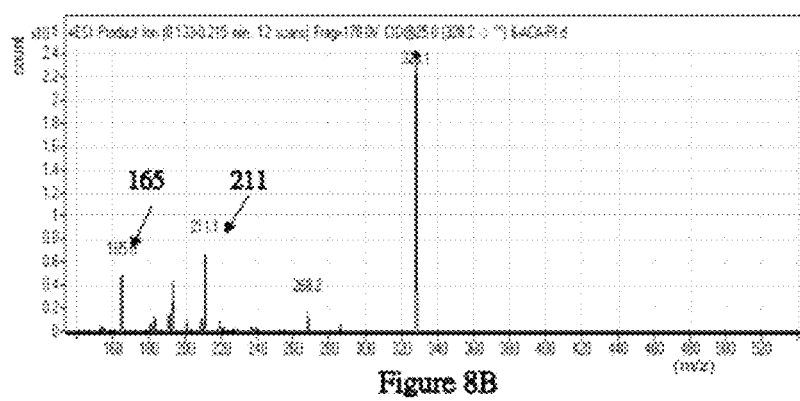
Figure 8C:
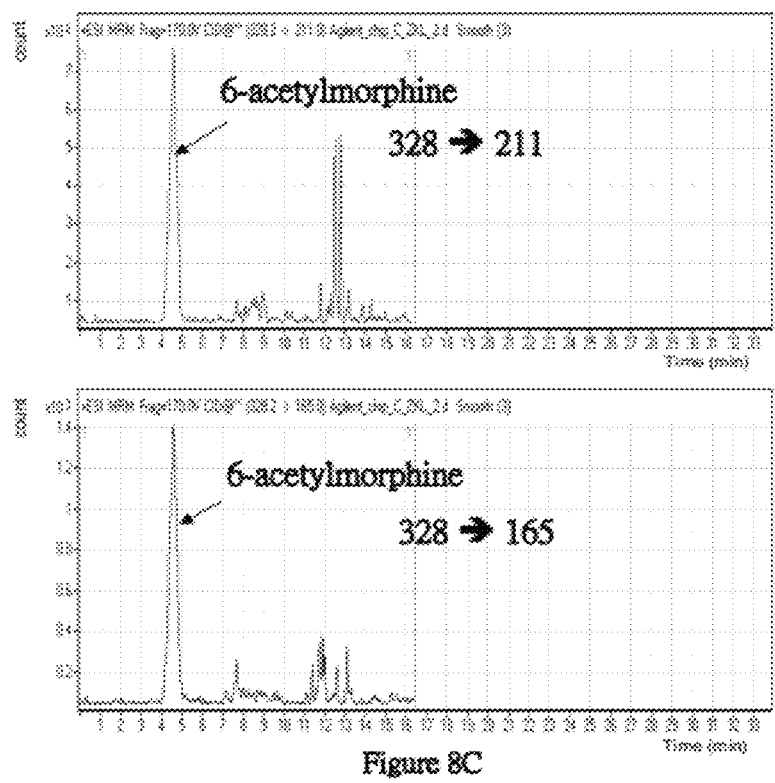
Figure 9A:
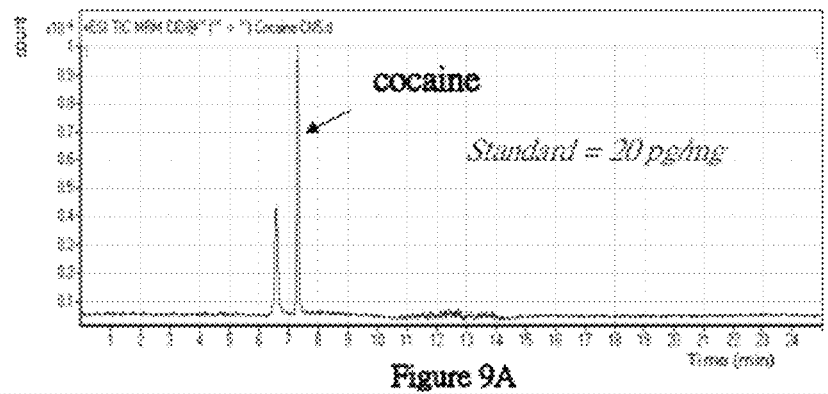
FIG. 9: HPLC-Chip-MS/MS cocaine MRM spectrum. (A) MRM spectrum from blank hair sample spiked with cocaine standard (20 pg/mg). (B) Calibration curve from blank hair sample spiked with cocaine standard (C) MRM spectrum from blank hair sample spiked with cocaine standard at the limit of quantification (LOQ) (0.5 pg/mg). (D) MRM spectrum from blank hair sample spiked with cocaine standard at the limit of detection (LOD) (0.1 pg/mg).
Figure 9B:
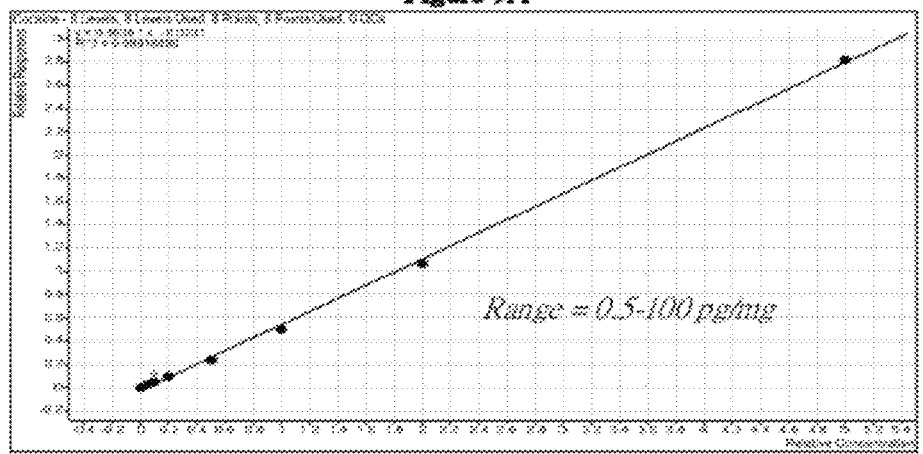
Figure 9C:
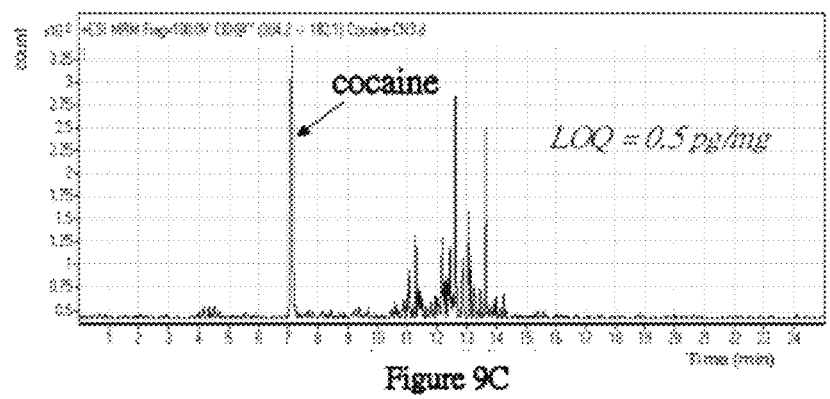
Figure 9D:
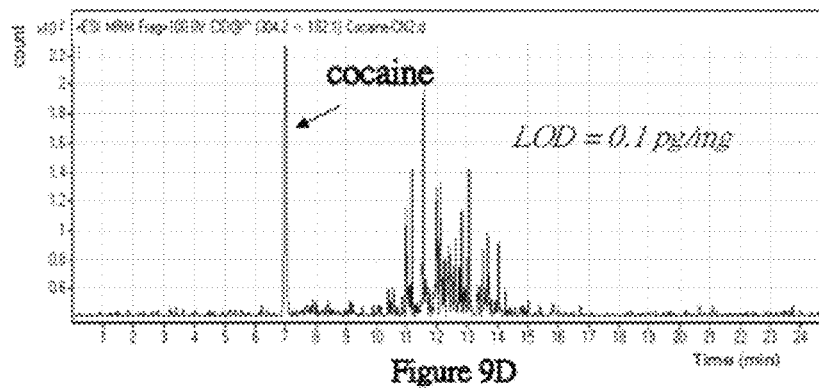

The detection of 6-acetylmorphine by HPLC-Chip-MS/MS is illustrated in FIGS. 7 and 8. FIG. 7 showed the MRM spectrum from blank hair sample spiked with 6-acetylmorphine standard, the calibration curve from blank hair sample spiked with 6-acetylmorphine standard, the limit of quantification (LOQ) and the limit of detection (LOD). FIG. 8 showed the chromatograms of hair analysis of 6-acetylmorphine by the method of the present invention. The presence of 6-acetylmorphine in the hair sample was shown by the presence of 6-acetylmorphine chromatographic peaks.

Example 5

Use of HPLC-Chip-MS/MS Method in Cocaine Detection

Same sample preparation, liquid chromatography conditions and mass spectrometry (MS) conditions as Example 1 are used in this example (except product ion detection). The product ion detection used in this example is 304.2>105.0, 304.2>182.1

Figure 10A:
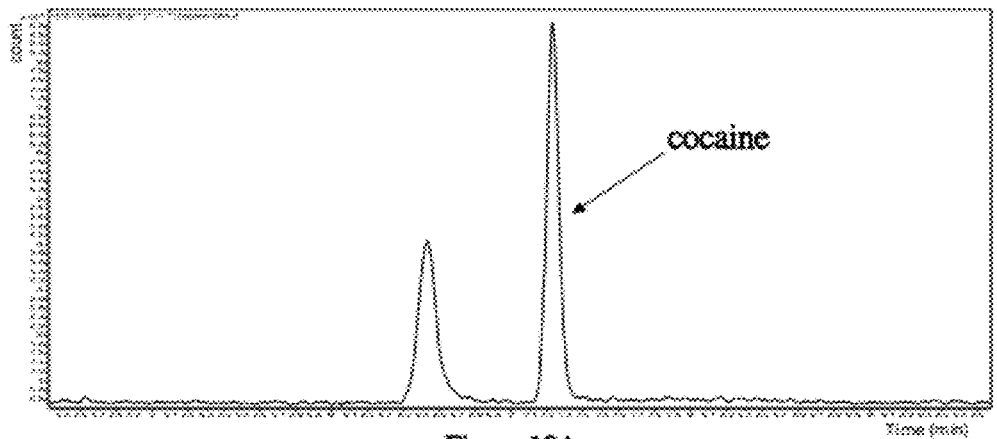
FIG. 10: HPLC-Chip-MS/MS analysis in hair of cocaine user. (A) Total ion count chromatogram of cocaine user hair sample. (B) MRM chromatogram of cocaine user hair sample. (C) Product ion MRM chromatogram of cocaine user hair sample.
Figure 10B:
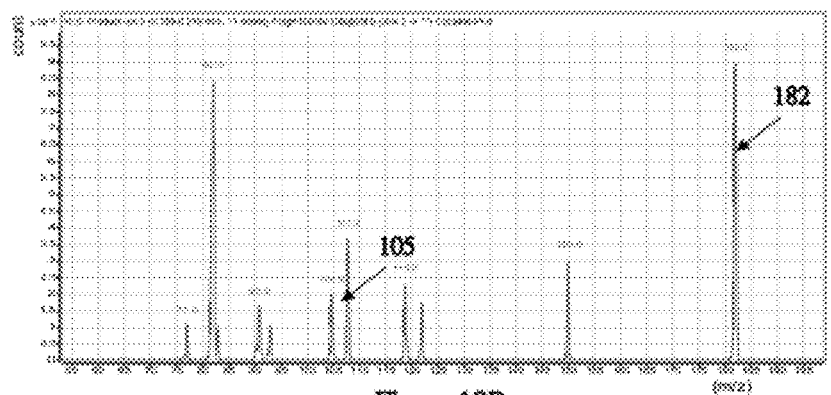
Figure 10C:
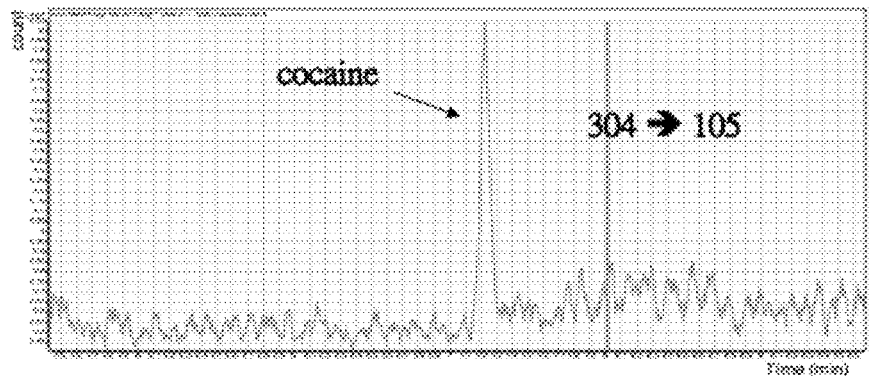
Figure 11A:
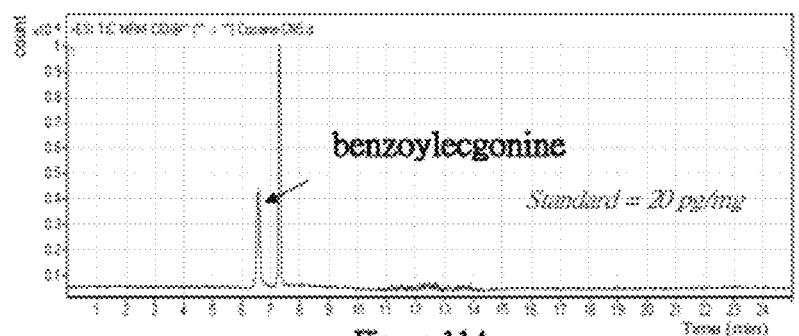
FIG. 11: HPLC-Chip-MS/MS benzoylecgonine MRM spectrum. (A) MRM spectrum from blank hair sample spiked with benzoylecgonine standard (20 pg/mg). (B) Calibration curve from blank hair sample spiked with benzoylecgonine standard. (C) MRM spectrum from blank hair sample spiked with benzoylecgonine standard at the limit of quantification (LOQ) (0.5 pg/mg). (D) MRM spectrum from blank hair sample spiked with benzoylecgonine standard at the limit of detection (LOD) (0.1 pg/mg).
Figure 11B:
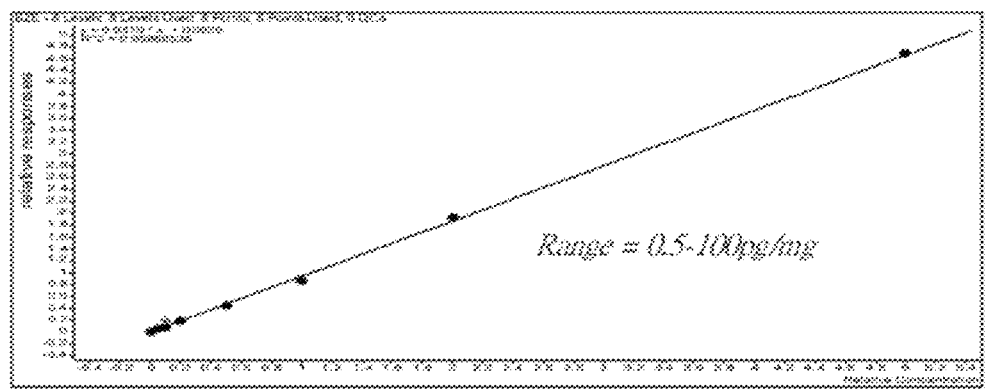
Figure 11C:
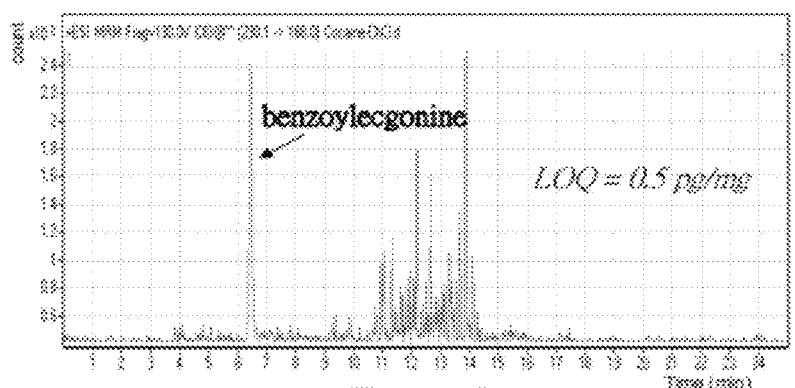
Figure 11D:
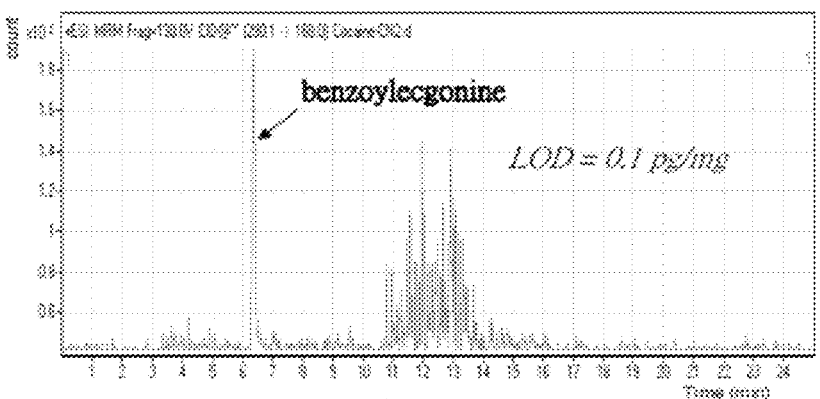

The detection of cocaine by the HPLC-Chip-MS/MS method is illustrated in FIGS. 9 and 10. FIG. 9 showed the MRM spectrum from blank hair sample spiked with cocaine standard, the calibration curve from blank hair sample spiked with cocaine standard, the limit of quantification (LOQ) and the limit of detection (LOD). FIG. 10 showed the chromatograms of hair analysis of cocaine by the method of the present invention. The presence of cocaine in the hair sample was shown by the presence of cocaine chromatographic peaks.

Example 6

Use of HPLC-Chip-MS/MS Method in Benzoylecgonine Detection

Same sample preparation, liquid chromatography conditions and mass spectrometry (MS) conditions as Example 1 are used in this example (except product ion detection). The product ion detection used in this example is 290.1>168.0, 290.1>105

Figure 12A:
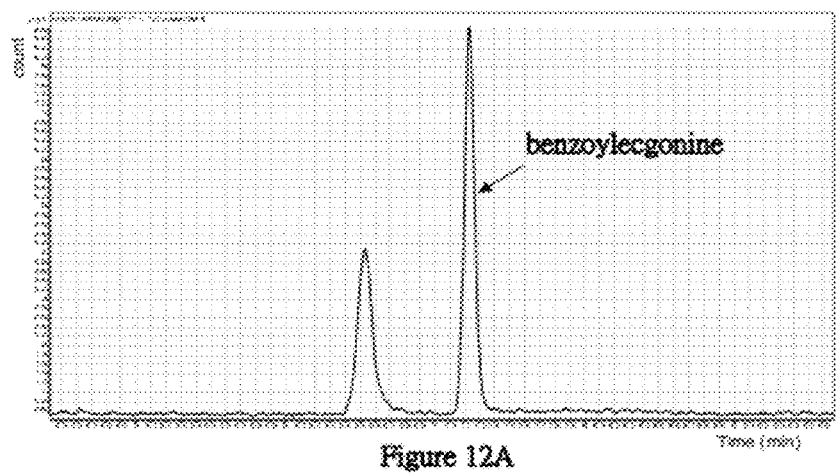
FIG. 12: HPLC-Chip-MS/MS analysis in hair of benzoylecgonine user. (A) Total ion count chromatogram of benzoylecgonine user hair sample. (B) MRM chromatogram of benzoylecgonine user hair sample. (C) Product ion MRM chromatogram of benzoylecgonine user hair sample.
Figure 12B:
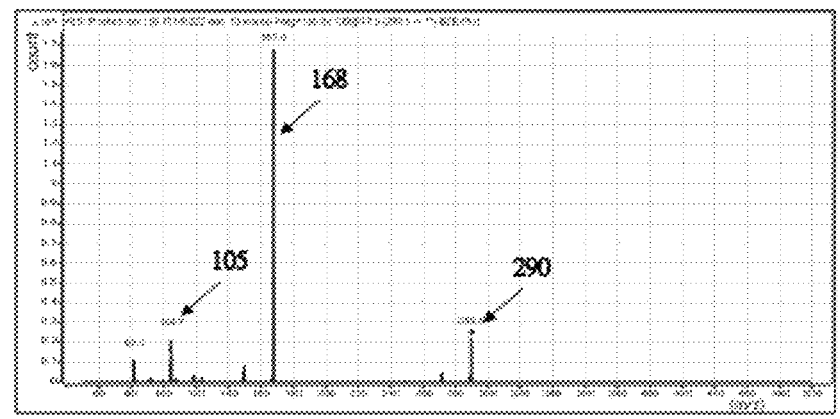
Figure 12C:
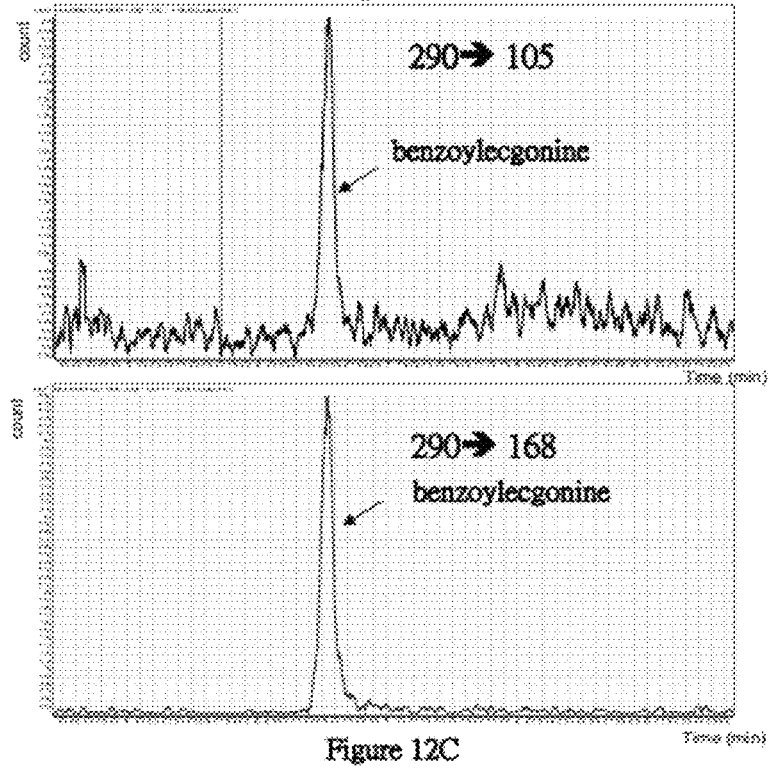
Figure 13A:
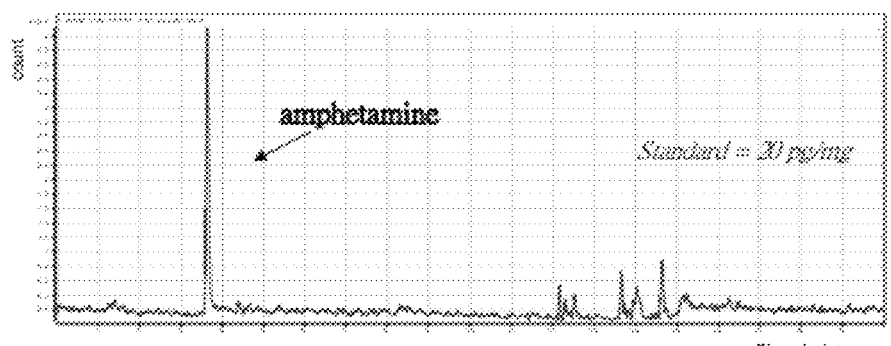
FIG. 13: HPLC-Chip-MS/MS amphetamine MRM spectrum. (A) MRM spectrum from blank hair sample spiked with amphetamine standard (20 pg/mg). (B) Calibration curve from blank hair sample spiked with amphetamine standard. (C) MRM spectrum from blank hair sample spiked with amphetamine standard at the limit of quantification (LOQ) (5 pg/mg). (D) MRM spectrum from blank hair sample spiked with amphetamine standard at the limit of detection (LOD) (2.5 pg/mg).
Figure 13B:
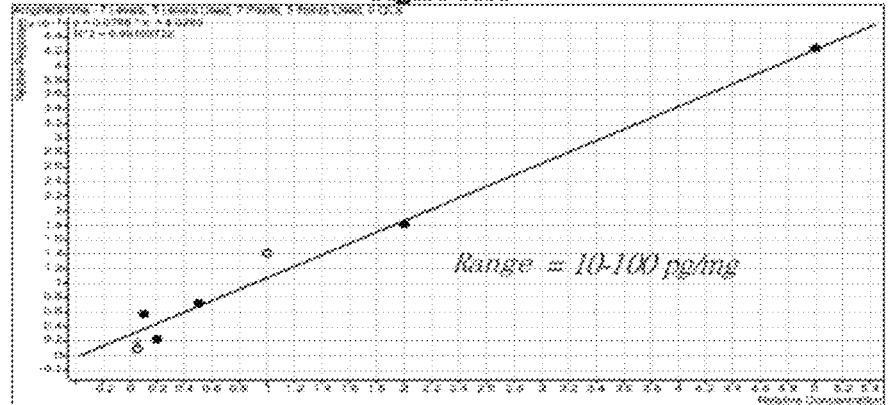
Figure 13C:
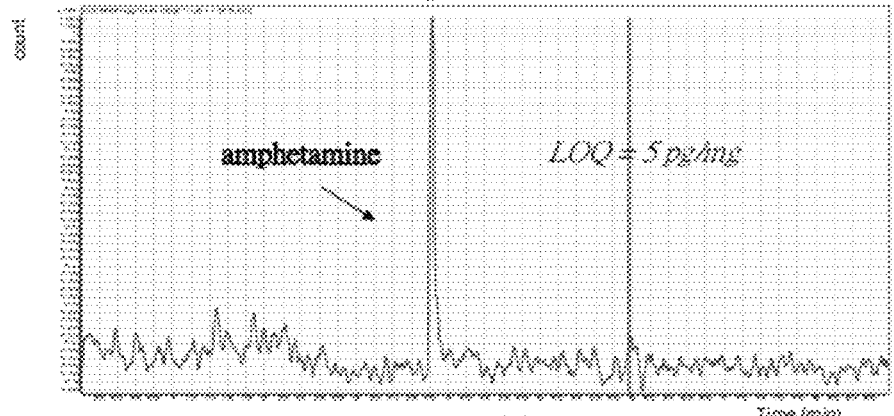
Figure 13D:
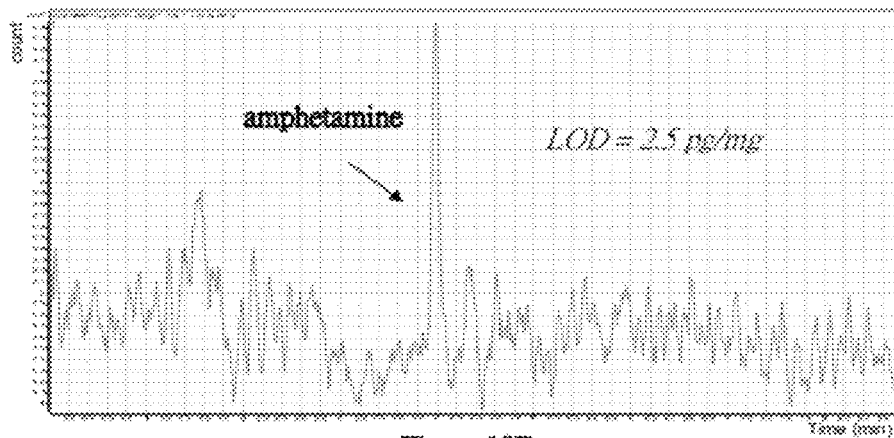

The detection of benzoylecgonine by the HPLC-Chip-MS/MS method is illustrated in FIGS. 11 and 12. FIG. 11 showed the MRM spectrum from blank hair sample spiked with benzoylecgonine standard, the calibration curve from blank hair sample spiked with benzoylecgonine standard, the limit of quantification (LOQ) and the limit of detection (LOD). FIG. 12 showed the chromatograms of hair analysis of benzoylecgonine by the method of the present invention. The presence of benzoylecgonine in the hair sample was shown by the presence of benzoylecgonine chromatographic peaks.

Example 7

Use of HPLC-Chip-MS/MS Method in Amphetamine Detection

Same sample preparation and mass spectrometry (MS) conditions as Example 1 are used in this example (except liquid chromatography conditions and product ion detection).

The liquid chromatography conditions used in this example include:
1. Instruments:
Agilent 1200 Series LC (Agilent Technologies, Waldbronn, Germany); Analytical column: Agilent chip Zorbax 80SB-Aq, 3.5 μm (Separation: 150 mm×75 μm, Enrichment: 9 mm, 160 nl); Chip is directly installed on the ion source with a micro-camera for monitoring of ionization spray. Chip cube includes chip holder for loading and ejecting chip, valve stator for solvent switching, linkage to micro-plate autosampler with capillary tube and nano electro-ionization spray for ionization. Data acquisition and analysis are performed by Mass Hunter ChemStation Softeare (version B01.03).
2. Capillary Pump Conditions:
Mobile phase A (0.1% formic acid in water); Mobile phase B (0.1% formic acid in acetonitrile); Injection volume: 2 μL; Flow rate: 1-6 μL/min (4 μL/min is preferred); Gradient: 0 min (3% B), 3 min (90% B), 5 min (90% B), 5.1 min (3% B), 25 min (3% B).
3. Nano Pump Conditions:
Mobile phase A (0.1% formic acid in water); Mobile phase B (0.1% formic acid in acetonitrile); Flow rate: 0.1-0.6 μL/min (0.4 μL/min is preferred); Gradient: 0 min (3% B), 3 min (3% B), 5 min (95% B), 12 min (95% B), 12.1 min (3% B), 25 min (3% B).
4. Chip Cube Conditions: Injection Flushing Volume (4 μL)

The product ion detection used in this example is 136.1>91.0, 136.1>119.0.

Figure 14A:
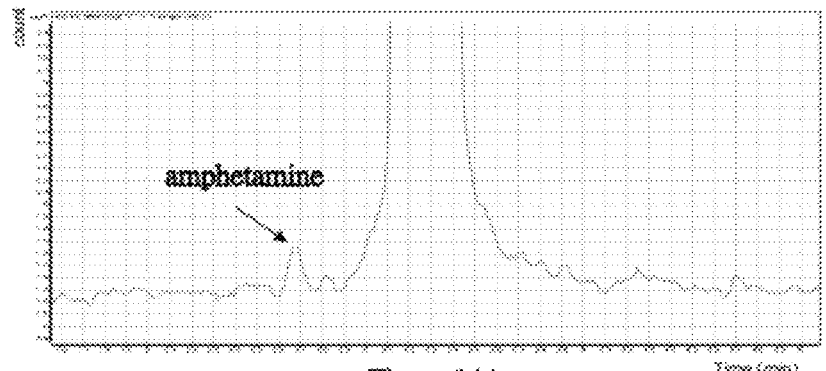
FIG. 14: HPLC-Chip-MS/MS analysis in hair of amphetamine user. (A) Total ion count chromatogram of amphetamine user hair sample. (B) MRM chromatogram of amphetamine user hair sample. (C) Product ion MRM chromatogram of amphetamine user hair sample.
Figure 14B:
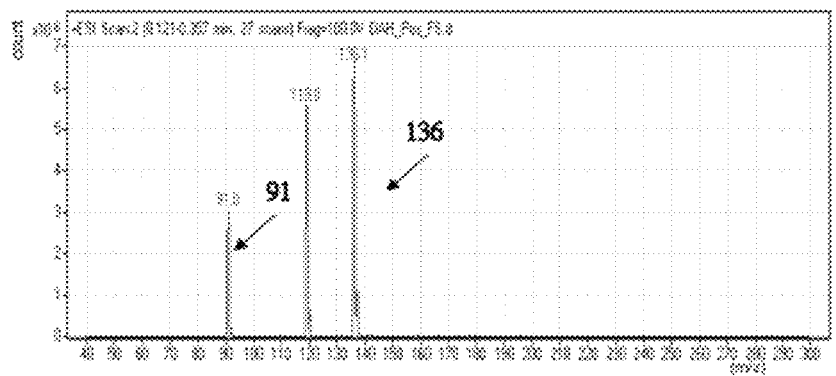
Figure 14C:
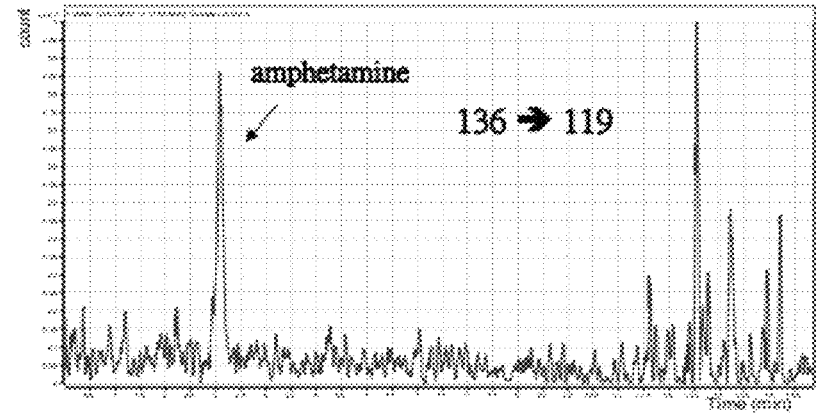
Figure 15A:
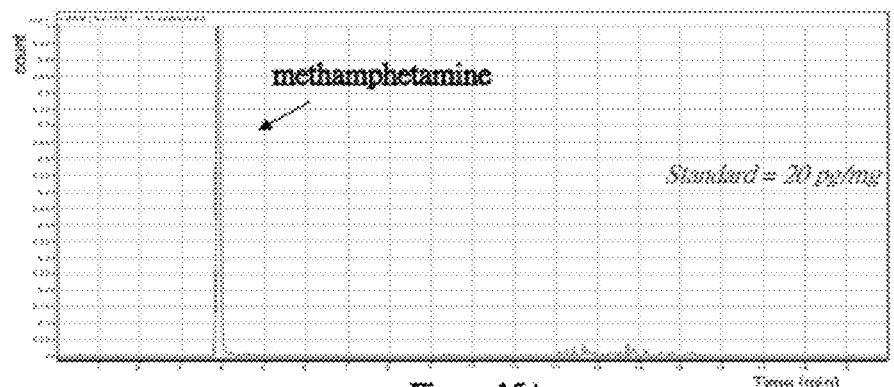
FIG. 15: HPLC-Chip-MS/MS methamphetamine MRM spectrum. (A). MRM spectrum from blank hair sample spiked with methamphetamine standard (20 pg/mg). (B) Calibration curve from blank hair sample spiked with methamphetamine standard. (C) MRM spectrum from blank hair sample spiked with methamphetamine standard at the limit of quantification (LOQ) (5 pg/mg). (D) MRM spectrum from blank hair sample spiked with methamphetamine standard at the limit of detection (LOD) (2.5 pg/mg).
Figure 15B:
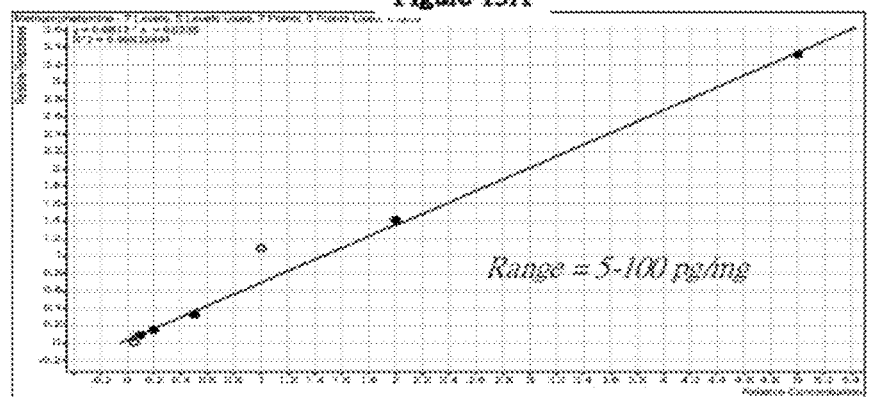
Figure 15C:
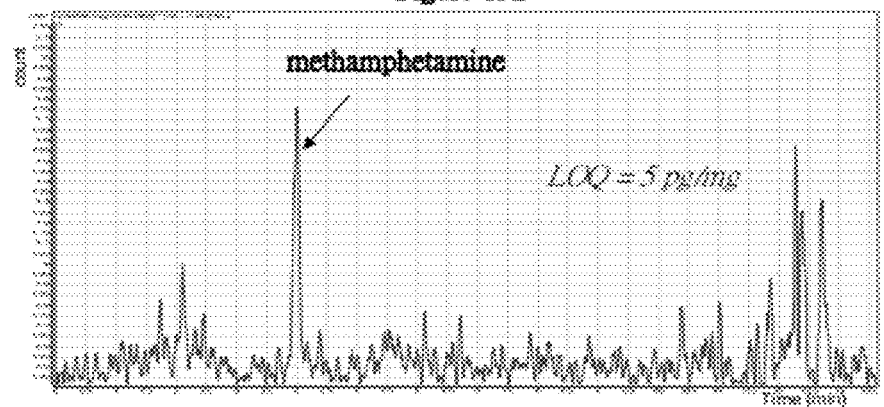
Figure 15D:
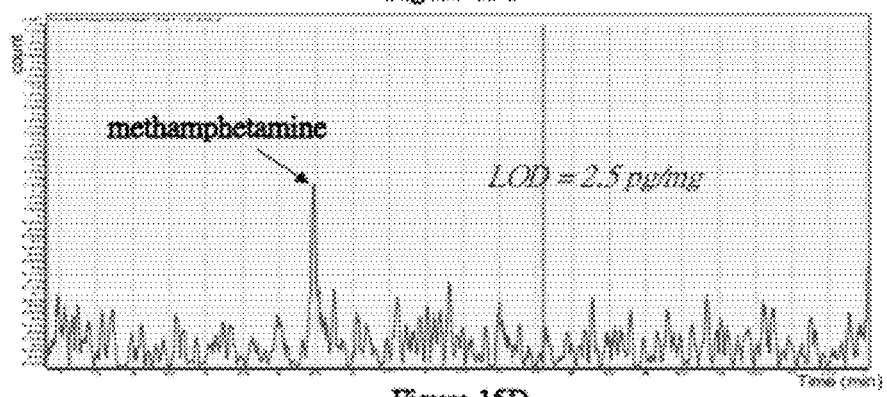
Figure 16A:
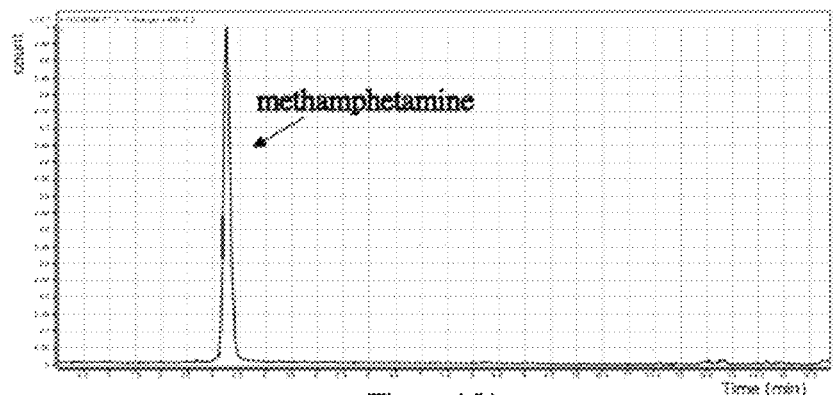
FIG. 16: HPLC-Chip-MS/MS analysis in hair of methamphetamine user. (A) Total ion count chromatogram of methamphetamine user hair sample. (B) MRM chromatogram of methamphetamine user hair sample. (C) Product ion MRM chromatogram of methamphetamine user hair sample.
Figure 16B:
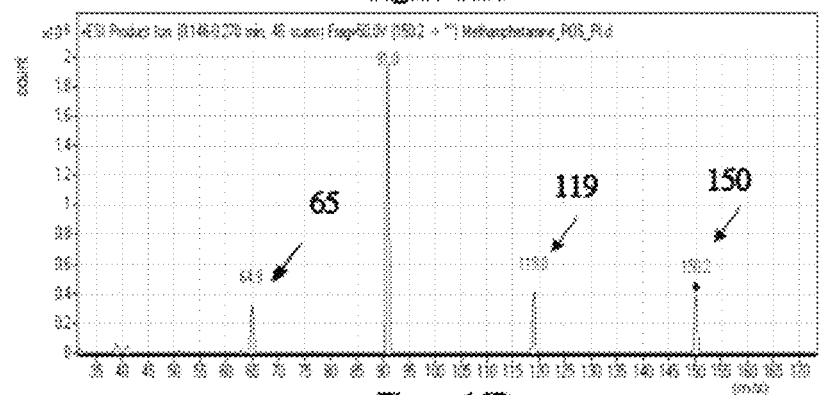
Figure 16C:
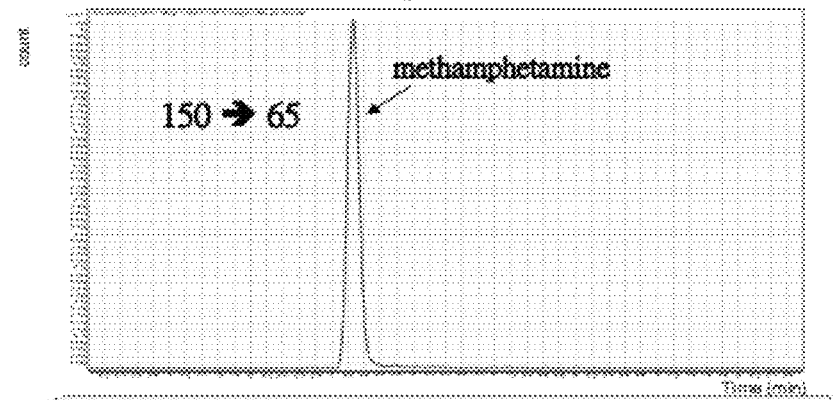
Figure 16C:
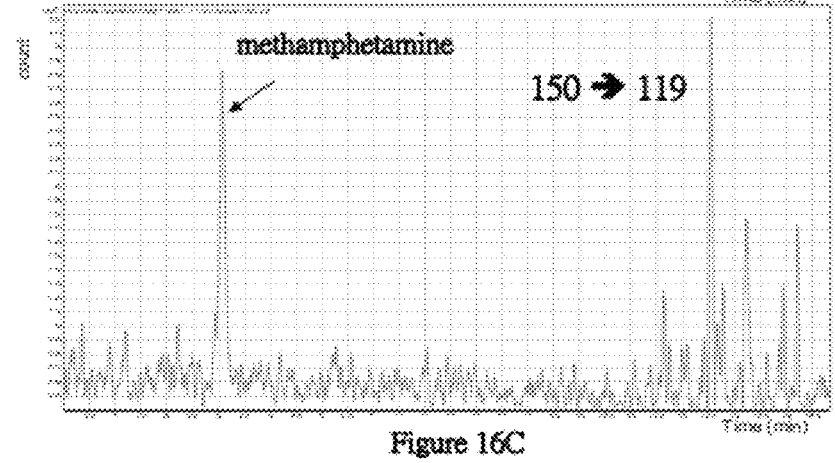
Figure 17A:
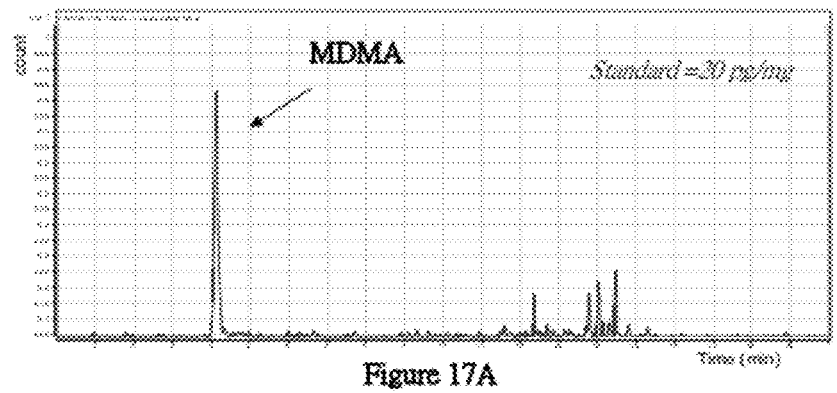
FIG. 17: HPLC-Chip-MS/MS MDMA MRM spectrum. (A) MRM spectrum from blank hair sample spiked with MDMA standard (20 pg/mg). (B) Calibration curve from blank hair sample spiked with MDMA standard. (C) MRM spectrum from blank hair sample spiked with MDMA standard at the limit of quantification (LOQ) (5 pg/mg). (D) MRM spectrum from blank hair sample spiked with MDMA standard at the limit of detection (LOD) (2.5 pg/mg).
Figure 17B:
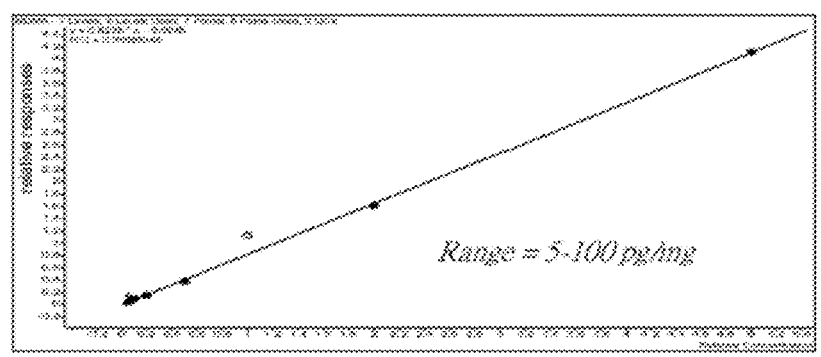
Figure 17C:
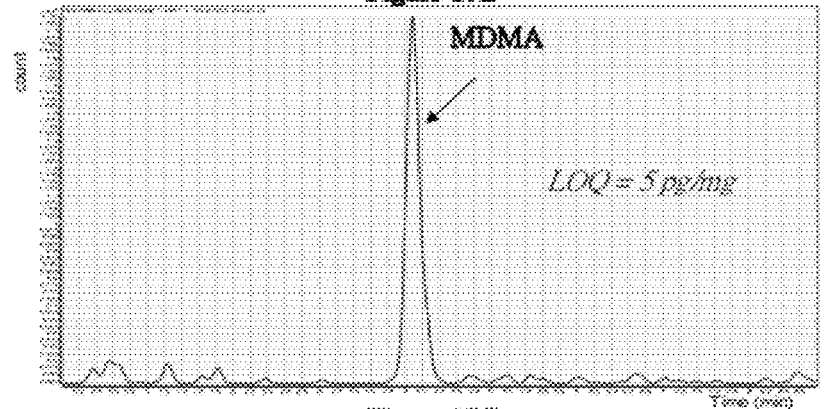
Figure 17D:
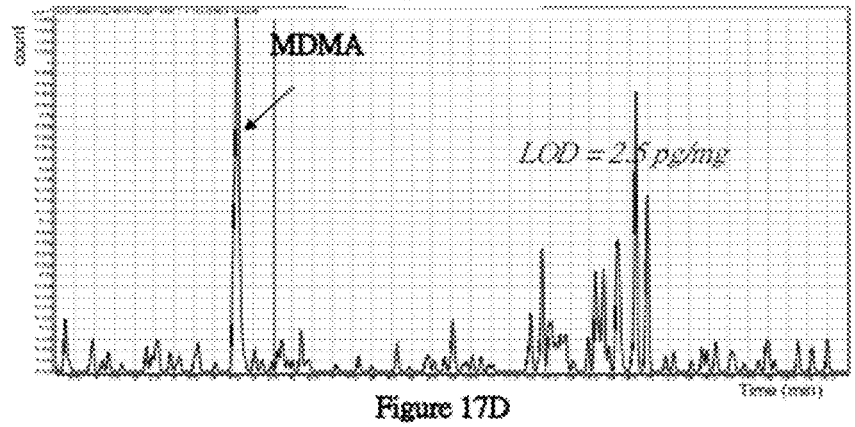

The detection of amphetamine by the HPLC-Chip-MS/MS method is illustrated in FIGS. 13 and 14. FIG. 13 showed the MRM spectrum from blank hair sample spiked with amphetamine standard, the calibration curve from blank hair sample spiked with amphetamine standard, the limit of quantification (LOQ) and the limit of detection (LOD). FIG. 14 showed the chromatograms of hair analysis of amphetamine by the method of the present invention. The presence of amphetamine in the hair sample was shown by the presence of amphetamine chromatographic peaks.

Example 8

Use of HPLC-Chip-MS/MS Method in Methamphetamine Detection

Same sample preparation, liquid chromatography conditions and mass spectrometry (MS) conditions as Example 7 are used in this example (except product ion detection). The product ion detection used in this example is 150.1>65.0, 150.1>91.0

The detection of methamphetamine by the HPLC-Chip-MS/MS method is illustrated in FIGS. 15 and 16. FIG. 15 showed the MRM spectrum from blank hair sample spiked with methamphetamine standard, the calibration curve from blank hair sample spiked with methamphetamine standard, the limit of quantification (LOQ) and the limit of detection (LOD). FIG. 16 showed the chromatograms of hair analysis of methamphetamine by the method of the present invention. The presence of methamphetamine in the hair sample was shown by the presence of methamphetamine chromatographic peaks.

Example 9

Use of HPLC-Chip-MS/MS Method in MDMA Detection

Same sample preparation, liquid chromatography conditions and mass spectrometry (MS) conditions as Example 7 are used in this example (except product ion detection). The product ion detection used in this example is 194.1>163.0, 194.1>105

Figure 18A:
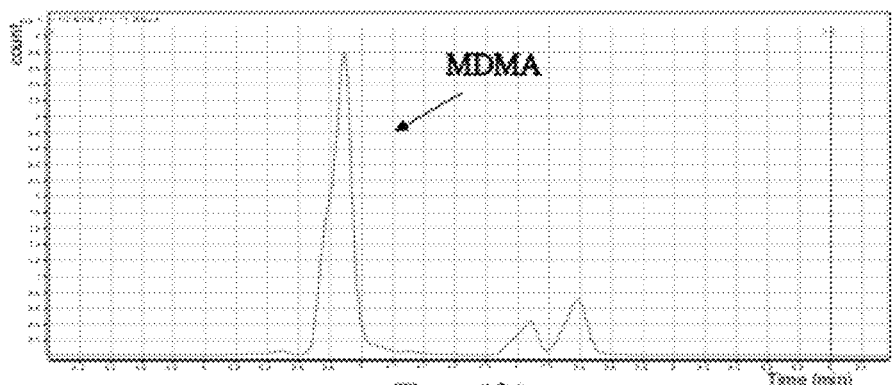
FIG. 18: HPLC-Chip-MS/MS analysis in hair of MDMA user. (A) Total ion count chromatogram of MDMA user hair sample. (B) MRM chromatogram of MDMA user hair sample. (C) Product ion MRM chromatogram of MDMA user hair sample.
Figure 18B:
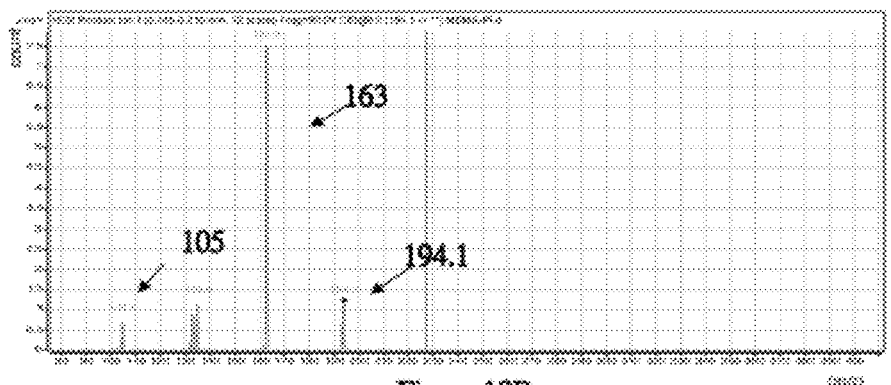
Figure 18C:
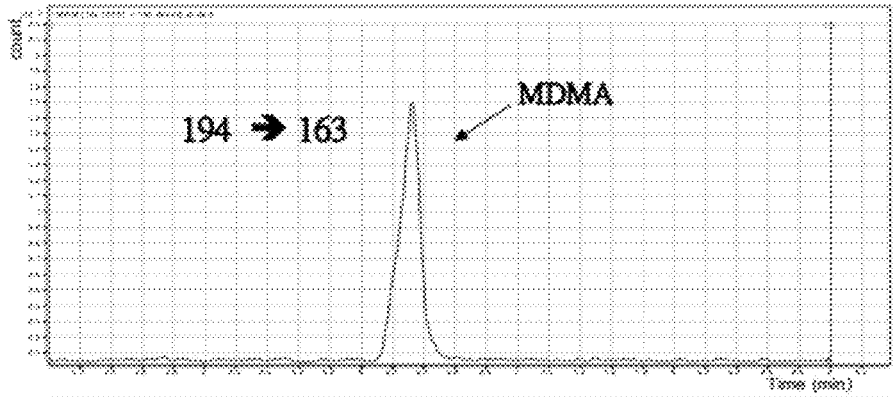
Figure 19A:
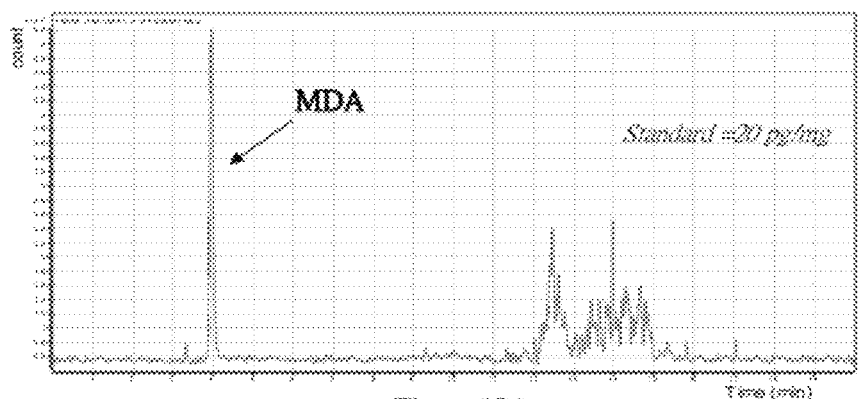
FIG. 19: HPLC-Chip-MS/MS MDA MRM spectrum. (A) MRM spectrum from blank hair sample spiked with MDA standard (20 pg/mg). (B) Calibration curve from blank hair sample spiked with MDA standard. (C) MRM spectrum from blank hair sample spiked with MDA standard at the limit of quantification (LOQ) (5 pg/mg). (D) MRM spectrum from blank hair sample spiked with MDA standard at the limit of detection (LOD) (2.5 pg/mg).
Figure 19B:
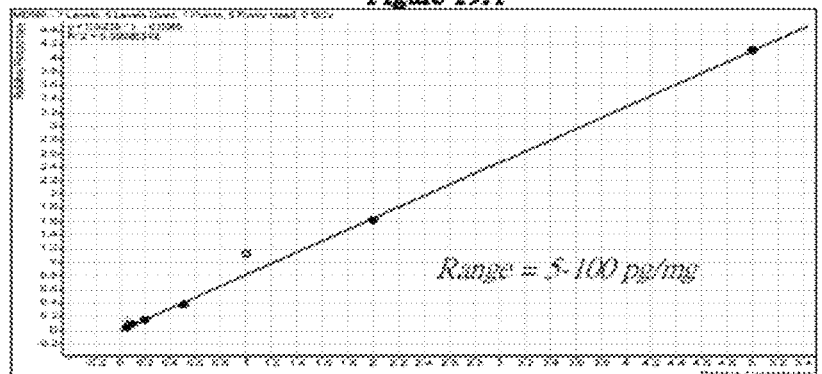
Figure 19C:
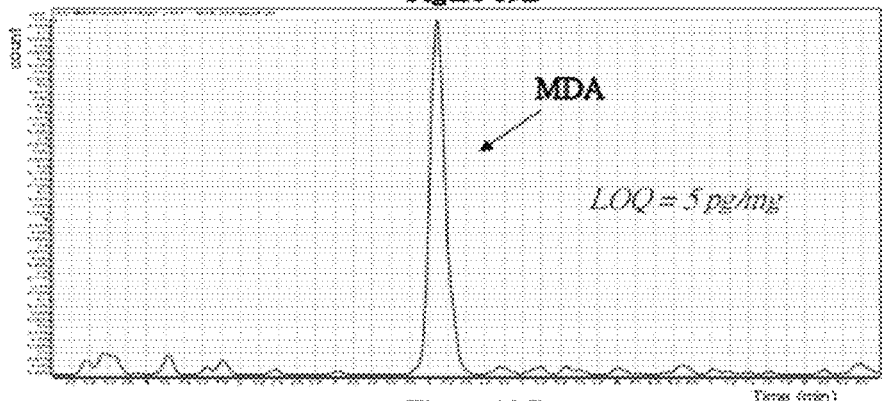
Figure 19D:
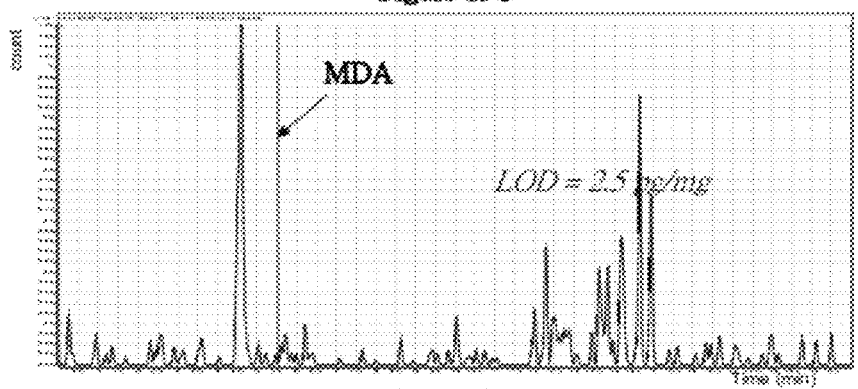
Figure 20A:
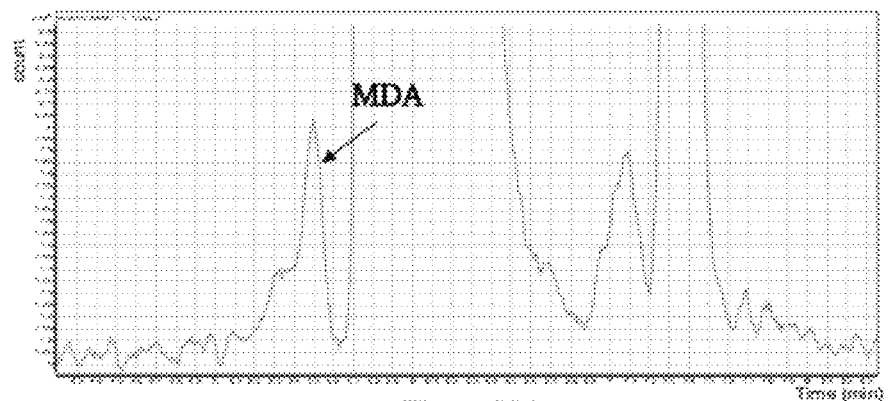
FIG. 20: HPLC-Chip-MS/MS analysis in hair of MDA user. (A) Total ion count chromatogram of MDA user hair sample. (B) MRM chromatogram of MDA user hair sample. (C) Product ion MRM chromatogram of MDA user hair sample.
Figure 20B:
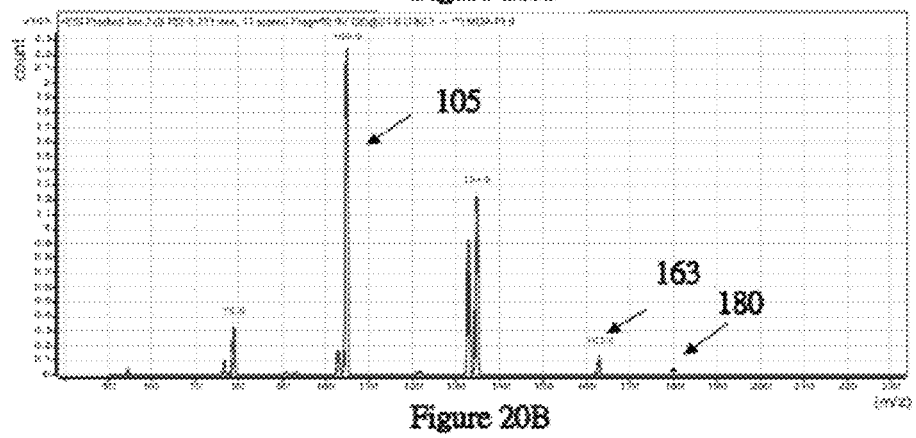
Figure 20C:
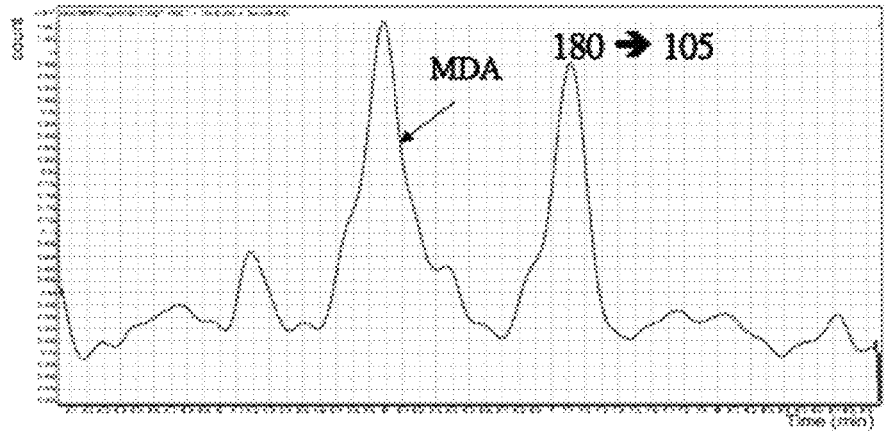
Figure 20C:
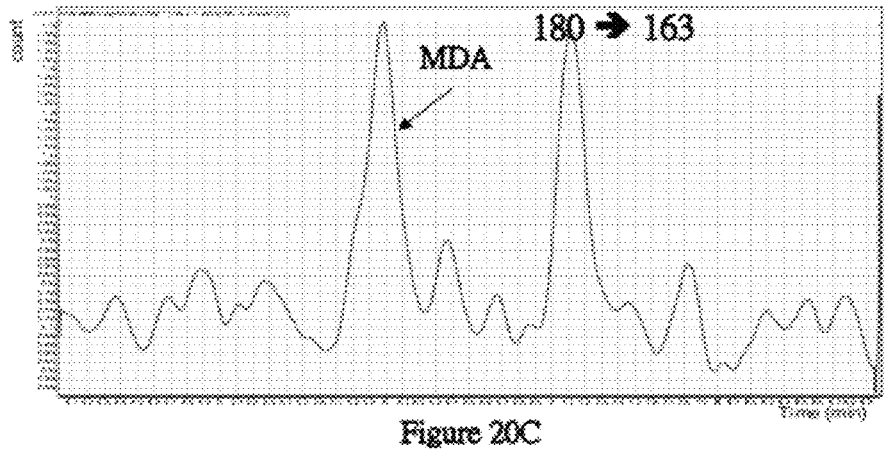
Figure 21A:
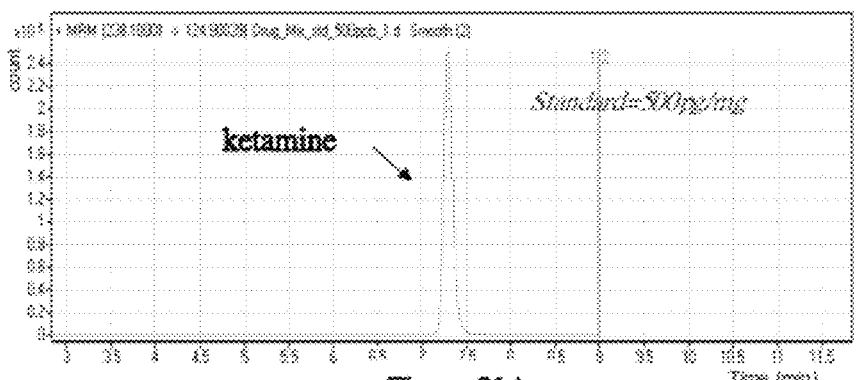
FIG. 21: HPLC-MS/MS ketamine MRM spectrum. (A) MRM spectrum from blank hair sample spiked with ketamine standard (500 pg/mg). (B) Calibration curve from blank hair sample spiked with ketamine standard. (C). MRM spectrum from blank hair sample spiked with ketamine standard at the limit of quantification (LOQ). (D) MRM spectrum from blank hair sample spiked with ketamine standard at the limit of detection (LOD).
Figure 21B:
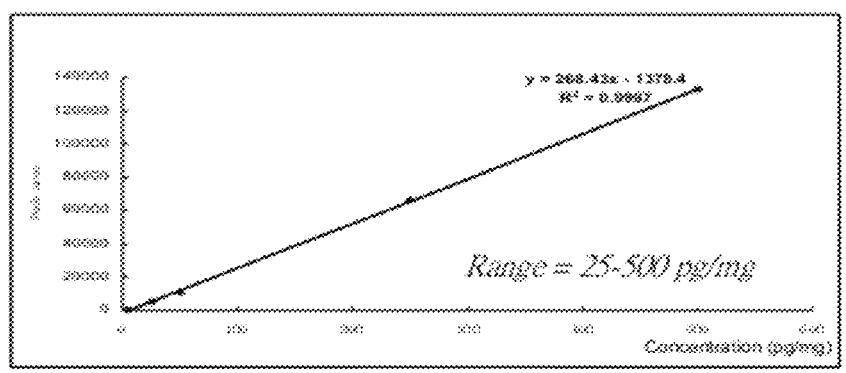
Figure 21C:
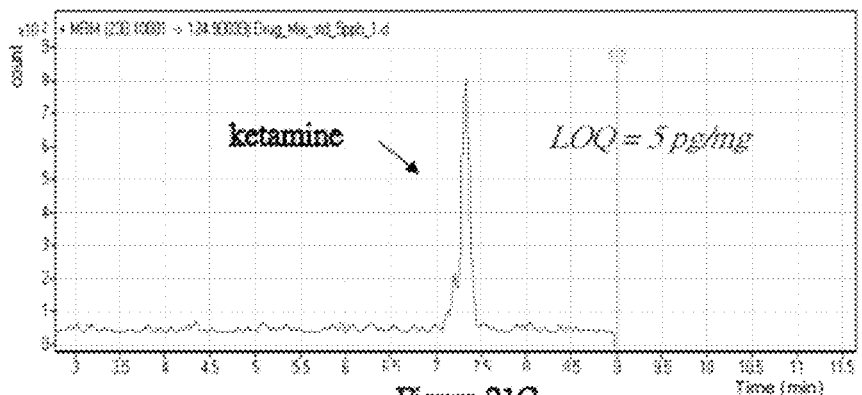
Figure 21D:
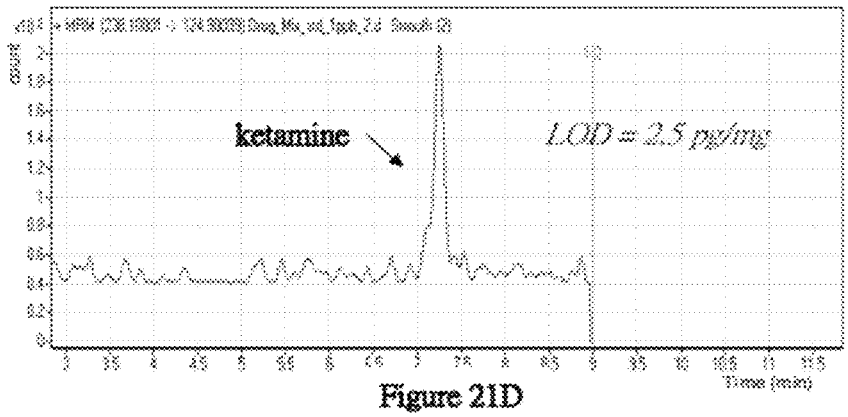
Figure 22A:
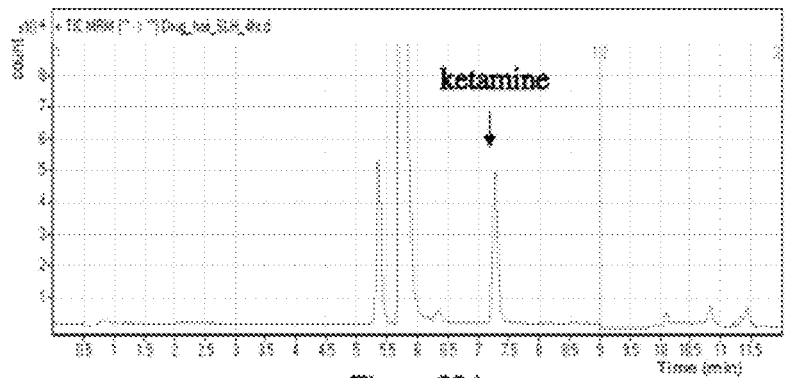
FIG. 22: HPLC-MS/MS analysis in hair of ketamine user. (A) Total ion count chromatogram of ketamine user hair sample. (B) MRM chromatogram of ketamine user hair sample. (C) Product ion MRM chromatogram of ketamine user hair sample.
Figure 22B:
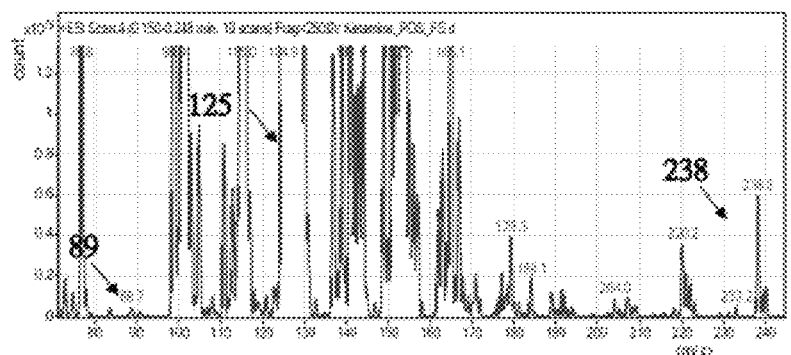
Figure 22C:
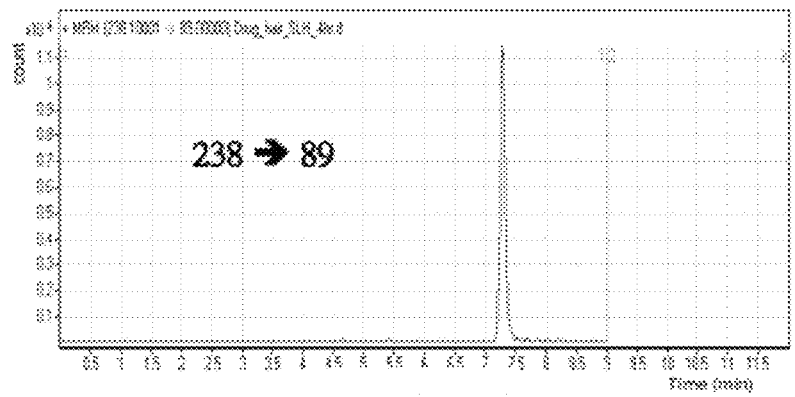
Figure 22C:
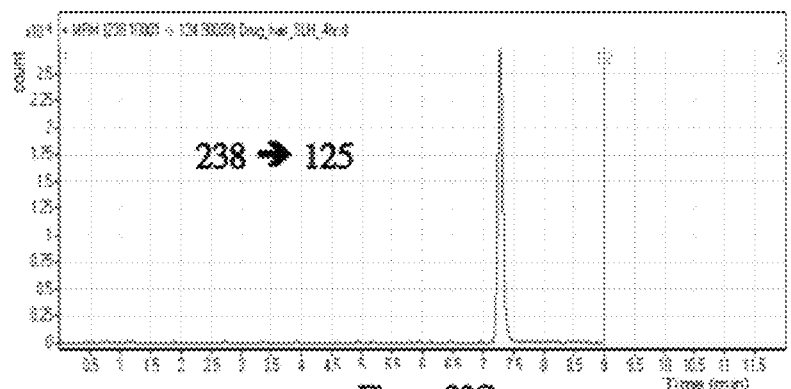
Figure 23A:
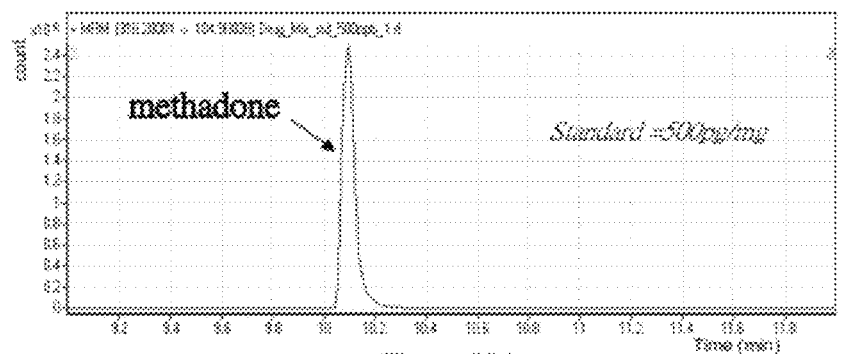
FIG. 23: HPLC-MS/MS methadone MRM spectrum. (A) MRM spectrum from blank hair sample spiked with methadone standard (500 pg/mg). (B) Calibration curve from blank hair sample spiked with methadone standard. (C). MRM spectrum from blank hair sample spiked with methadone standard at the limit of quantification (LOQ). (D) MRM spectrum from blank hair sample spiked with methadone standard at the limit of detection (LOD).
Figure 23B:
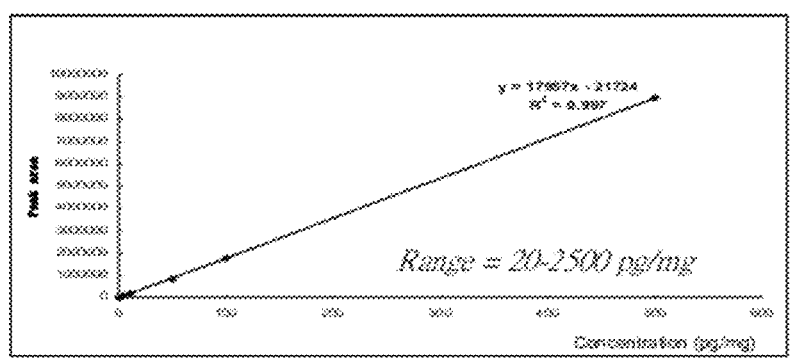
Figure 23C:
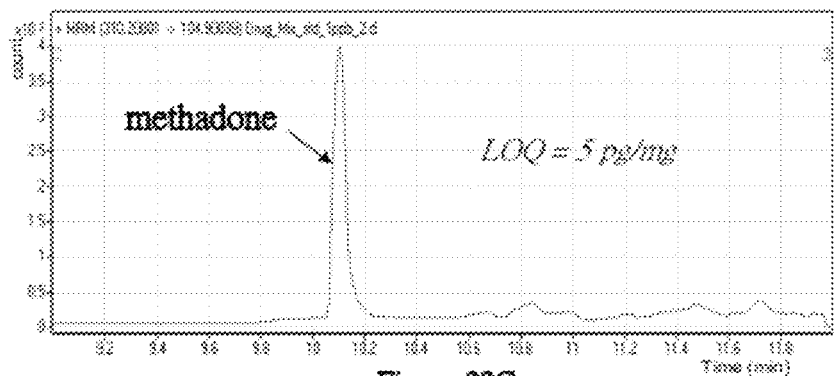
Figure 23D:
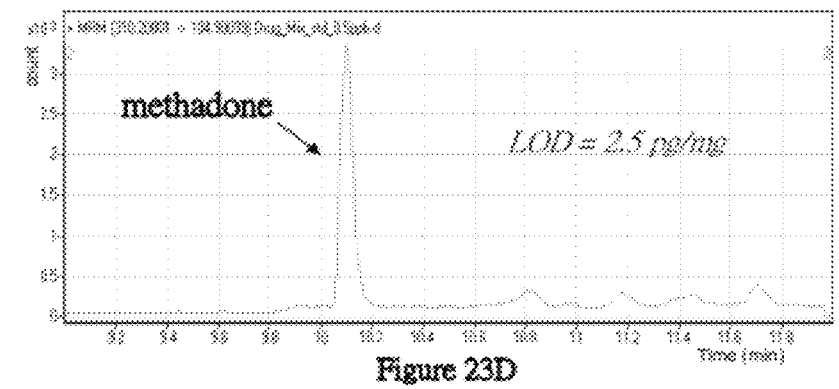
Figure 24A:
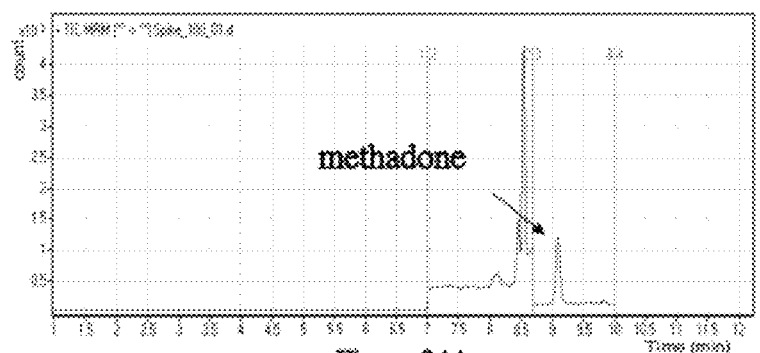
FIG. 24: HPLC-MS/MS analysis in hair of methadone user. (A) Total ion count chromatogram of methadone user hair sample. (B) MRM chromatogram of methadone user hair sample. (C) Product ion MRM chromatogram of methadone user hair sample.
Figure 24B:
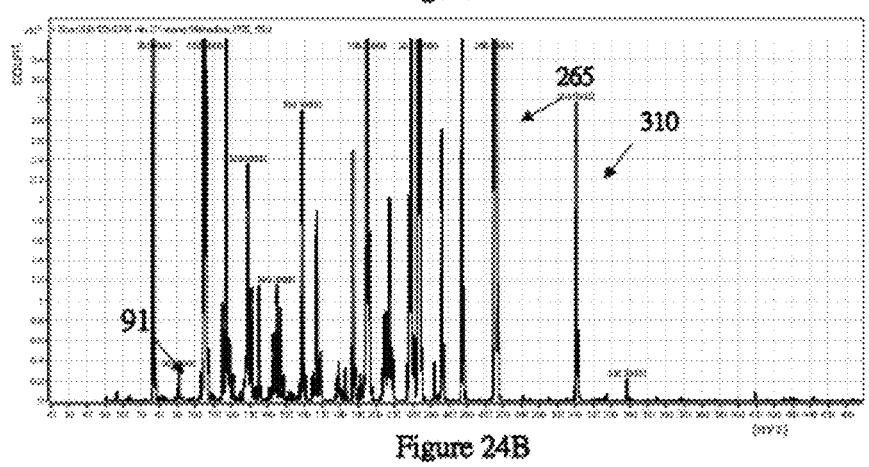
Figure 24C:
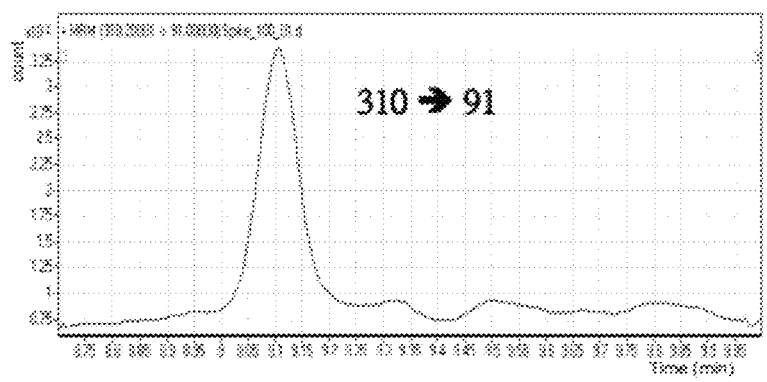
Figure 24C:
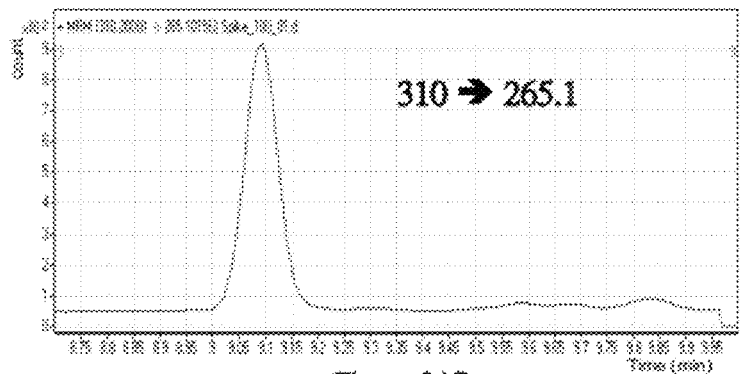
Figure 25A:
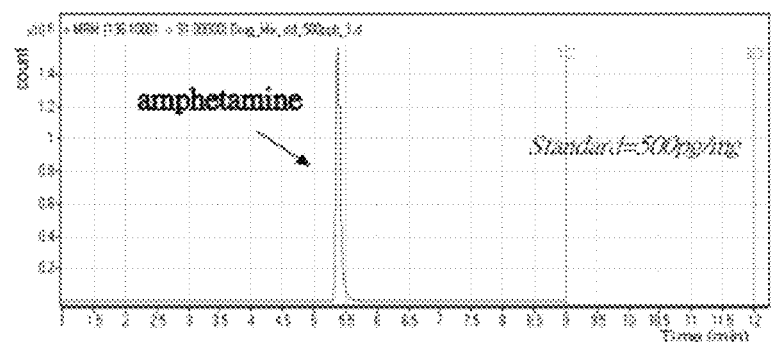
FIG. 25: HPLC-Chip-MS/MS amphetamine MRM spectrum. (A) MRM spectrum from blank hair sample spiked with amphetamine standard (500 pg/mg). (B) Calibration curve from blank hair sample spiked with amphetamine standard. (C) MRM spectrum from blank hair sample spiked with amphetamine standard at the limit of quantification (LOQ). (D) MRM spectrum from blank hair sample spiked with amphetamine standard at the limit of detection (LOD).
Figure 25B:
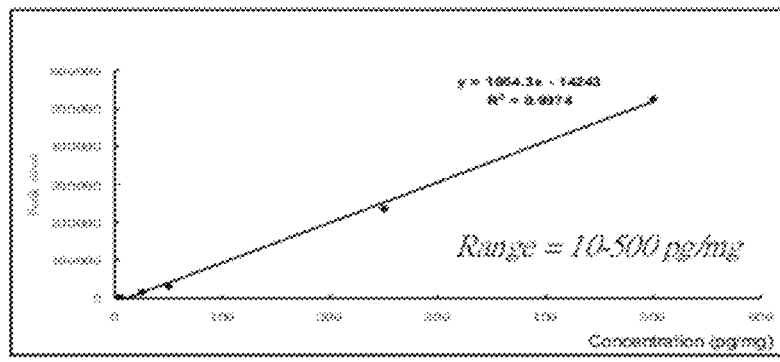
Figure 25C:
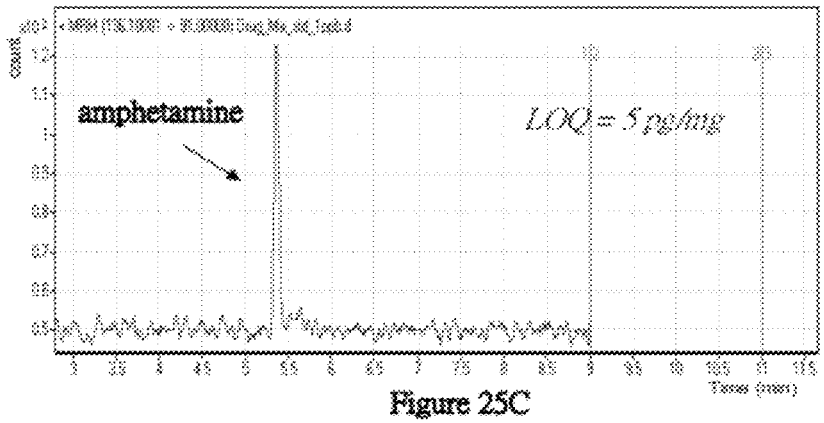
Figure 25D:
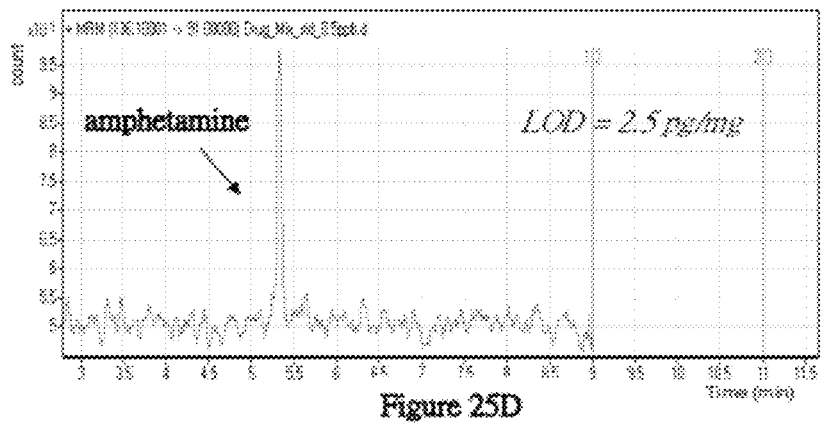
Figure 26A:
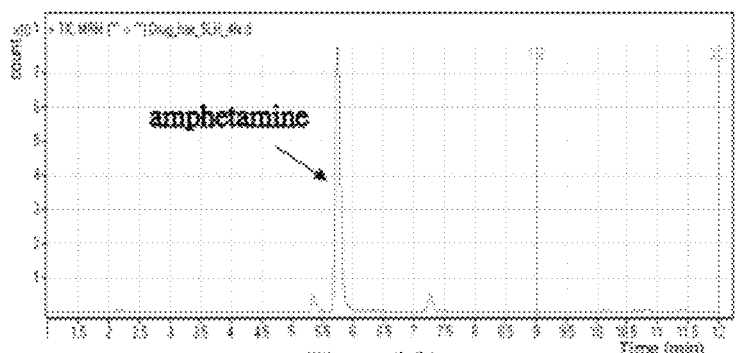
FIG. 26: HPLC-MS/MS analysis in hair of amphetamine user. (A) Total ion count chromatogram of amphetamine user hair sample. (B) MRM chromatogram of amphetamine user hair sample. (C) Product ion MRM chromatogram of amphetamine user hair sample.
Figure 26B:
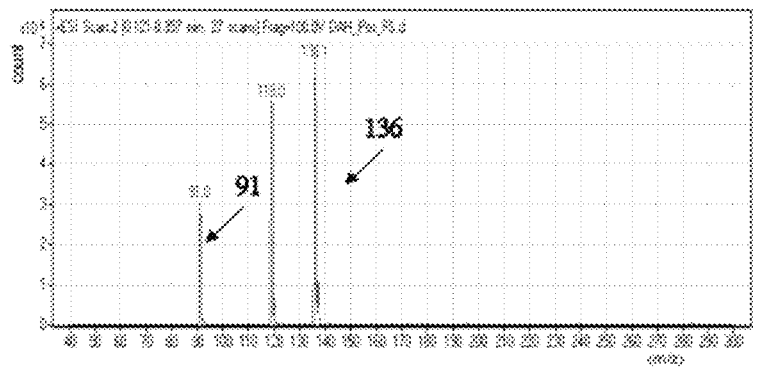
Figure 26C:
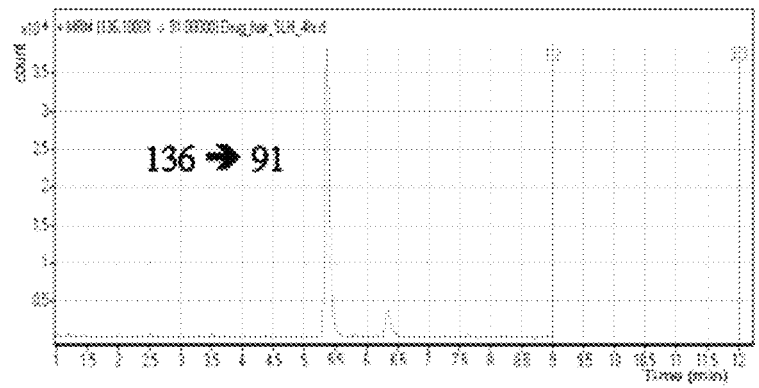
Figure 26C:
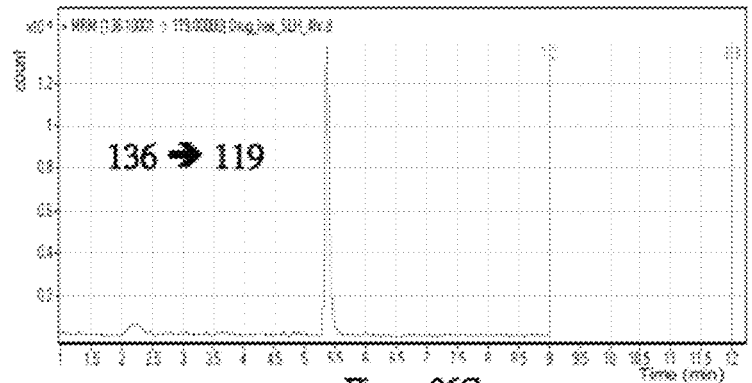
Figure 27A:
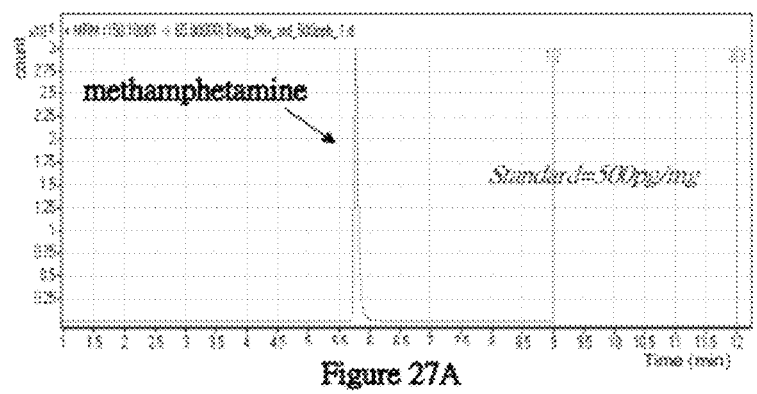
FIG. 27: HPLC-MS/MS methamphetamine MRM spectrum. (A). MRM spectrum from blank hair sample spiked with methamphetamine standard (500 pg/mg). (B) Calibration curve from blank hair sample spiked with methamphetamine standard. (C) MRM spectrum from blank hair sample spiked with methamphetamine standard at the limit of quantification (LOQ). (D) MRM spectrum from blank hair sample spiked with methamphetamine standard at the limit of detection (LOD).
Figure 27B:
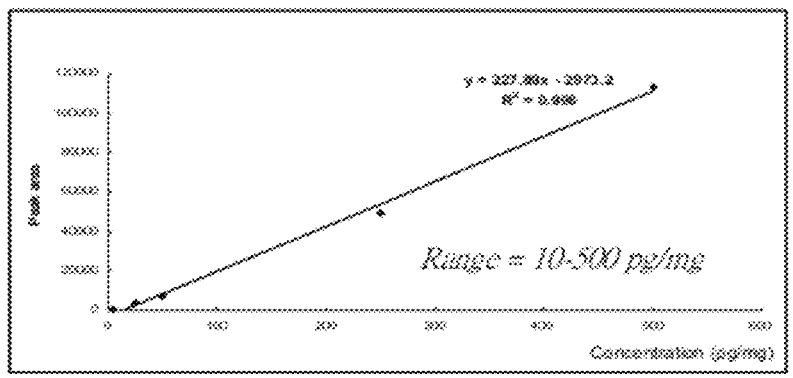
Figure 27C:
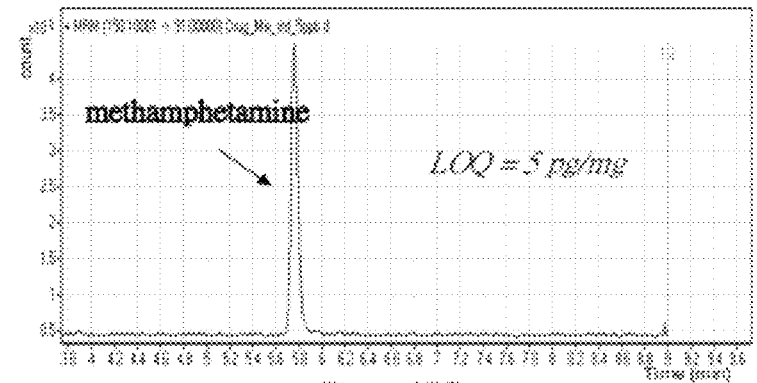
Figure 27D:
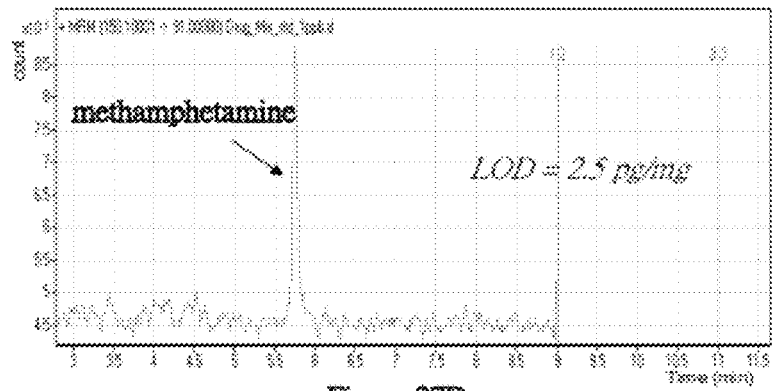
Figure 28A:
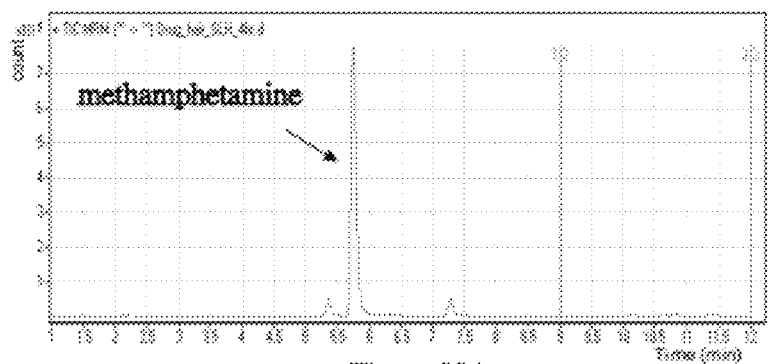
FIG. 28: HPLC-MS/MS analysis in hair of methamphetamine user. (A) Total ion count chromatogram of methamphetamine user hair sample. (B) MRM chromatogram of methamphetamine user hair sample. (C) Product ion MRM chromatogram of methamphetamine user hair sample.
Figure 28B:
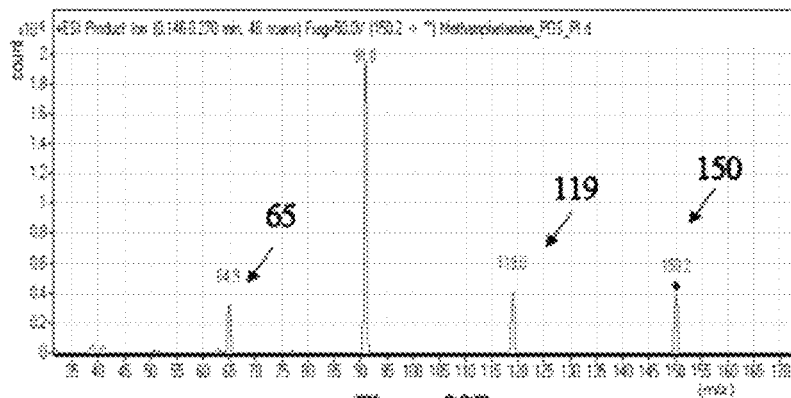
Figure 28C:
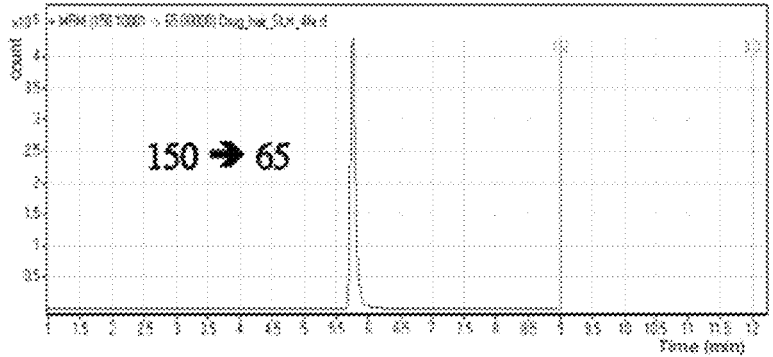
Figure 28C:
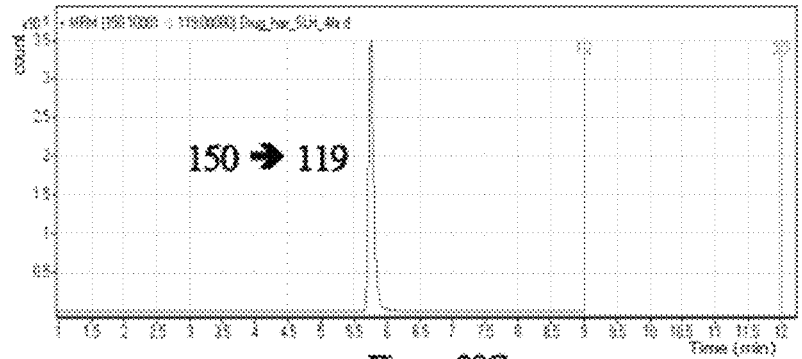

The detection of MDMA by the HPLC-Chip-MS/MS method is illustrated in FIGS. 17 and 18. FIG. 17 showed the MRM spectrum from blank hair sample spiked with MDMA standard, the calibration curve from blank hair sample spiked with MDMA standard, the limit of quantification (LOQ) and the limit of detection (LOD). FIG. 18 showed the chromatograms of hair analysis of MDMA by the method of the present invention. The presence of MDMA in the hair sample was shown by the presence of MDMA chromatographic peaks.

Example 10

Use of HPLC-Chip-MS/MS Method in MDA Detection

Same sample preparation, liquid chromatography conditions and mass spectrometry (MS) conditions as Example 7 are used in this example (except product ion detection). The product ion detection used in this example is 180.1>135.0, 180.1>163.0

The detection of MDA by the HPLC-Chip-MS/MS method is illustrated in FIGS. 19 and 20. FIG. 19 showed the MRM spectrum from blank hair sample spiked with MDA standard, the calibration curve from blank hair sample spiked with MDA standard, the limit of quantification (LOQ) and the limit of detection (LOD). FIG. 20 showed the chromatograms of hair analysis of MDA by the method of the present invention. The presence of MDA in the hair sample was shown by the presence of MDA chromatographic peaks.

Example 11

Comparison of Conventional GC-MS/MS Method with HPLC-Chip-MS/MS Method on Sensitivity

TABLE 1

Comparison of Conventional GC-MS/MS with HPLC-Chip-MS/MS Method on Sensitivity

| Drug | Limit of detection (LOD) (pg/mg) | | Limit of quantification (LOQ) (pg/mg) | |
|---|---|---|---|---|
| | HPLC-Chip-MS/MS | GC-MS/MS | HPLC-Chip-MS/MS | GC-MS/MS |
| Ketamine | 0.1 | 200 | 0.1 | 500 |
| Methadone | 0.1 | 200 | 0.1 | 800 |
| Morphine | 2 | 10 | 2 | 500 |
| 6-acetyl-morphine | 2 | 30 | 2 | 500 |
| Cocaine | 0.1 | 20 | 0.1 | 50 |
| Benzoylecgonine | 0.1 | 15 | 0.1 | 50 |
| Amphetamine | 0.3 | 160 | 0.3 | 500 |
| Methamphetamine | 0.1 | 100 | 0.1 | 500 |
| MDMA | 0.1 | 200 | 0.1 | 500 |
| MDA | 0.5 | 300 | 0.5 | 800 |

Example 12

Use of HPLC-MS/MS Method in Ketamine Detection

Sample preparation is the same as that in Example 1.

Liquid chromatography conditions used in this example include:

a. Instruments: Agilent 1200 Series LC (Agilent Technologies, Waldbronn, Germany); Analytical column: Agilent ZORBAX Eclipse C18, 3.5 µm, 2.1×100 mm b. Capillary Pump Conditions: Flow rate: 0.1-0.6 mL/min (0.4 mL/min is preferred)

| Time (min) | 0.1% formic acid in water | 0.1% formic acid in acetonitrile |
|---|---|---|
| 0.0-2.0 | 95 | 5 |
| 2.0-2.6 | 10 | 13 |
| 2.6-8.0 | 15.5 | 84.5 |
| 8.0-8.1 | 20 | 80 |
| 8.1-11.0 | 20 | 80 |

3. Mass Spectrometry (MS) Conditions:

Instruments: Agilent QQQ 6410A; Drying gas temperature: 325° C.; Drying gas flow: 10 L/min; Capillary voltage: 4000V; Nebulizer: 35 psi; Polarity: Positive ion mode; Scan mode: Multiple Reaction Monitoring (MRM); Product ion detection: 238.1>125.0, 238.1>89.0

The detection of ketamine by the HPLC-MS/MS method is illustrated in FIGS. 21 and 22. FIG. 21 showed the MRM spectrum from blank hair sample spiked with ketamine standard, the calibration curve from blank hair sample spiked with ketamine standard, the limit of quantification (LOQ) and the limit of detection (LOD). FIG. 22 showed the chromatograms of hair analysis of ketamine by the method of the present invention. The presence of ketamine in the hair sample was shown by the presence of ketamine chromatographic peaks.

Example 13

Use of HPLC-MS/MS Method in Methadone Detection

Same sample preparation, liquid chromatography conditions and mass spectrometry (MS) conditions as Example 12 are used in this example (except product ion detection). The product ion detection used in this example is 310.2>265.1, 310.2>91.0

The detection of methadone by the HPLC-MS/MS method is illustrated in FIGS. 23 and 24. FIG. 23 showed the MRM spectrum from blank hair sample spiked with methadone standard, the calibration curve from blank hair sample spiked with methadone standard, the limit of quantification (LOQ) and the limit of detection (LOD). FIG. 24 showed the chromatograms of hair analysis of methadone by the method of the present invention. The presence of methadone in the hair sample was shown by the presence of methadone chromatographic peaks.

Example 14

Use of HPLC-MS/MS Method in Amphetamine Detection

Same sample preparation, liquid chromatography conditions and mass spectrometry (MS) conditions as Example 12 are used in this example (except product ion detection). The product ion detection used in this example is 136.1>91.0, 136.1>119.0

The detection of amphetamine by the HPLC-MS/MS method is illustrated in FIGS. 25 and 26. FIG. 25 showed the MRM spectrum from blank hair sample spiked with amphetamine standard, the calibration curve from blank hair sample spiked with amphetamine standard, the limit of quantification (LOQ) and the limit of detection (LOD). FIG. 26 showed the chromatograms of hair analysis of amphetamine by the method of the present invention. The presence of amphetamine in the hair sample was shown by the presence of amphetamine chromatographic peaks.

Example 15

Use of HPLC-MS/MS Method in Methamphetamine Detection

Same sample preparation, liquid chromatography conditions and mass spectrometry (MS) conditions as Example 12 are used in this example (except product ion detection). The product ion detection used in this example is 150.1>65.0, 150.1>119.0

The detection of methamphetamine by the HPLC-MS/MS method is illustrated in FIGS. 27 and 28. FIG. 27 showed the MRM spectrum from blank hair sample spiked with methamphetamine standard, the calibration curve from blank hair sample spiked with methamphetamine standard, the limit of quantification (LOQ) and the limit of detection (LOD). FIG. 28 showed the chromatograms of hair analysis of methamphetamine by the method of the present invention. The presence of methamphetamine in the hair sample was shown by the presence of methamphetamine chromatographic peaks.

Example 16

Hair Analysis in Blind Samples

Blind test is a crucial examination step to the competency of the method of the present invention. With the application of different conditions in Examples 1-8, ketamine, methadone, morphine, heroin, cocaine, benzoylecgonine, amphetamine and methamphetamine were analyzed in eight blind samples. Table 2 showed that the HPLC-Chip-Ms/MS method can be used to differentiate drug users from non-drug users, and identify the type of drug used.

Example 17

Drug Analysis of Abuser in Different Hair Segments

Parent drug and its metabolites normally appear in hair after 5-7 day once administered. Hair normally grows at 0.75-1 cm/month. Drug taking habit or history can be reflected by analysis in different hair segments.

Figure 29:
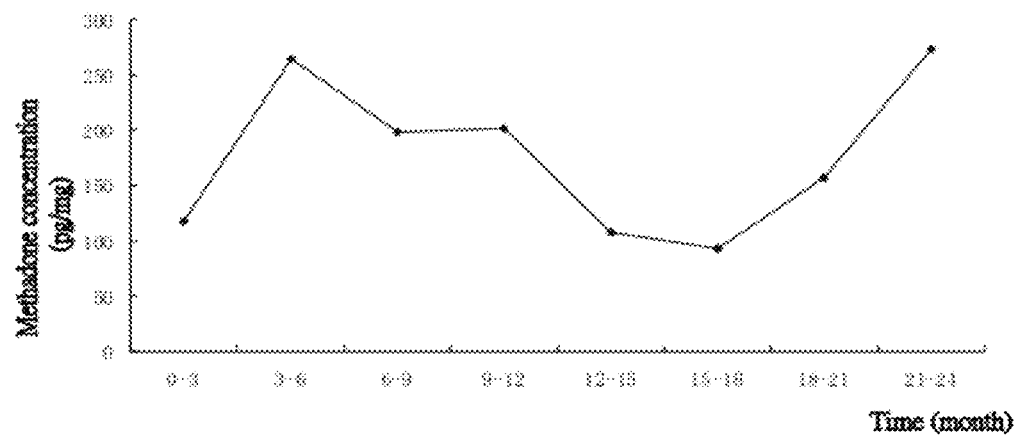
FIG. 29: The change of methamphetamine concentration in different hair length of drug abuser.
Figure 30:
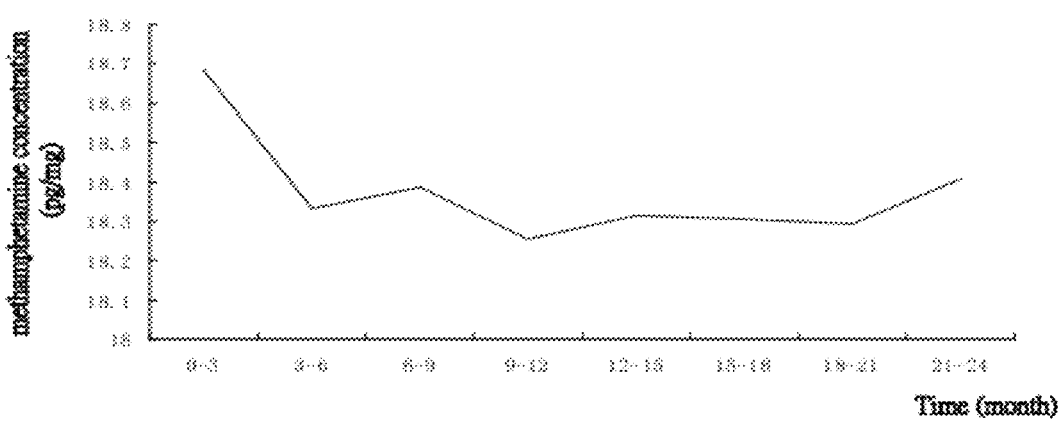
FIG. 30: The change of methadone concentration in different hair length of drug abuser.
Figure 31:
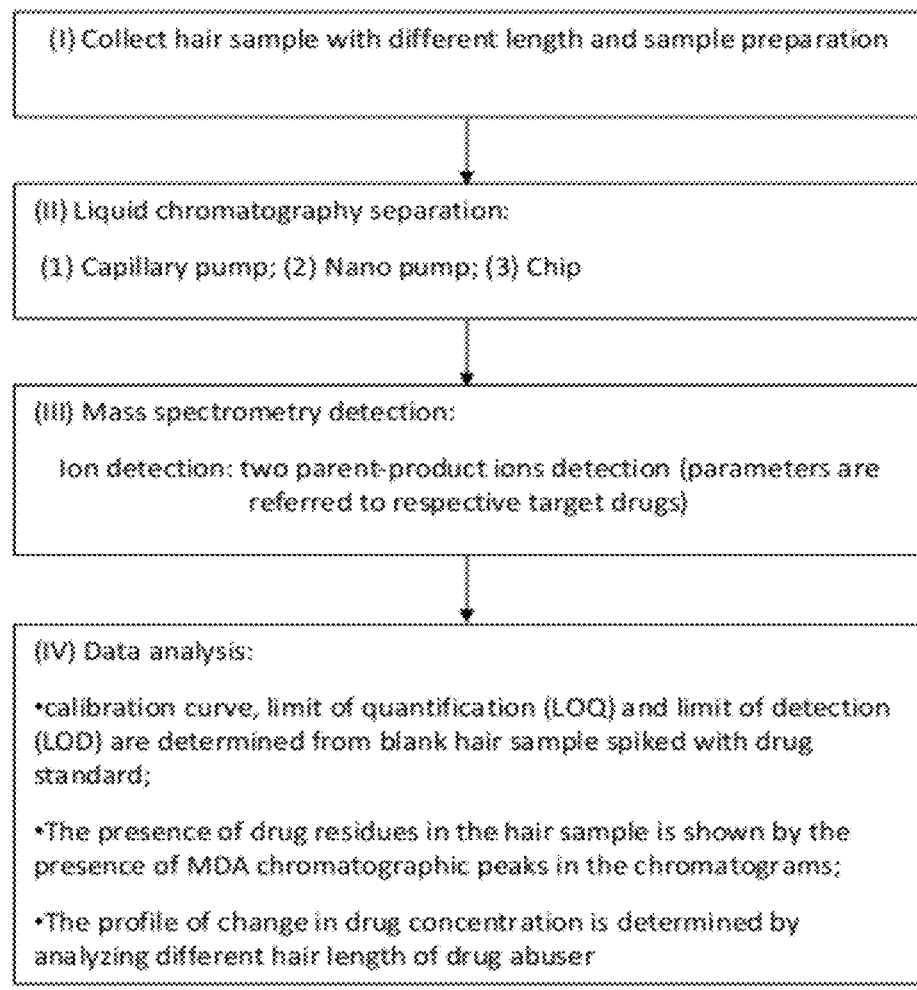
FIG. 31: The flow chart of HPLC-Chip-MS/MS detection method for drug residues in human hair.

Hair specimens were collected and cut into different lengths. With the application of different conditions in Examples 1-8, drug distribution in different hair segments was illustrated (FIGS. 29 and 30). Tables 3 and 4, and FIGS. 29 and 30 illustrated the drug taking history of methamphetamine and methadone from the target drugs detected in different hair segments which the different lengths of the collected hair segments are proportional to the time history of drug user.

TABLE 3

Proportional Relationship between Hair Length and Time History

| | Hair segment sample no. | | | | | | | |
|---|---|---|---|---|---|---|---|---|
| | 1 | 2 | 3 | 4 | 5 | 6 | 7 | 8 |
| Hair length (cm) | 0-4 | 4-8 | 8-12 | 12-16 | 16-20 | 20-24 | 24-28 | 28-32 |
| Time (month) | 0-3 | 3-6 | 6-9 | 9-12 | 12-15 | 15-18 | 18-21 | 21-24 |

TABLE 4

Detection of Methamphetamine and Methadone Concentration in Different Hair Segments

| | Hair segment sample no. | | | | | | | |
|---|---|---|---|---|---|---|---|---|
| | 1 | 2 | 3 | 4 | 5 | 6 | 7 | 8 |
| Methamphetamine (pg/mg) | 117.6 | 263.6 | 198.2 | 201.1 | 107.3 | 920 | 156.3 | 273.5 |
| Methadone (pg/mg) | 18.7 | 18.3 | 18.4 | 18.3 | 18.3 | 18.3 | 18.3 | 18.4 |

Example 18

Detection of Drug Residues by HPLC-Chip-MS/MS Method in Urine Sample of Drug Abuser (1) Sample Preparation:
The pH of urine sample was adjusted to pH 9-10 by adding 1 mol/L of NaOH. Sample was loaded on GDX403 column for

TABLE 2

Blind test results

| Test no. | Drug abuser? (Y/N) | Type of drug claimed* | Morphine | Heroin (6-acetylmorphine) | Amphetamine | Methamphetamine | Methadone |
|---|---|---|---|---|---|---|---|
| 1 | Y | amphetamines | | | + | + | |
| 2 | N | | | | | | |
| 3 | Y | heroin, methadone | | + | | | + |
| 4 | N | | | | | | |
| 5 | N | | | | | | |
| 6 | Y | heroin, methadone | + | + | | + | + |
| 7 | Y | amphetamines, methamphetamine | | | + | + | |
| 8 | N | | | | | | |

(*Provided by Shenzhen Detoxification and Rehabilitation Center)

solid phase extraction. Sample was eluted with dichloromethane. After dryness, sample was resuspended by 50 μL of acetonitrile for analysis.

(2) Liquid Chromatography Conditions:
(i) Instruments:
Agilent 1200 Series LC (Agilent Technologies, Waldbronn, Germany); Analytical column: Agilent chip Zorbax 80SB-C18, 5 μm (Separation: 150 mm×75 μm, Enrichment: 25 mm, 500 nl); Chip is directly installed on the ion source with a micro-camera for monitoring of ionization spray. Chip cube includes chip holder for loading and ejecting chip, valve stator for solvent switching, linkage to micro-plate autosampler with capillary tube and nano electro-ionization spray for ionization. Data acquisition and analysis are performed by Mass Hunter ChemStation Softeare (version B01.03).
(ii) Capillary Pump Conditions:
Mobile phase A (0.1% formic acid in water); Mobile phase B (0.1% formic acid in acetonitrile); Injection volume: 2 μL; Flow rate: 1-6 μL/min (4 μL/min is preferred); Gradient: 0 min (3% B), 3 min (90% B), 5 min (90% B), 5.1 min (3% B), 25 min (3% B).
(iii) Nano Pump Conditions:
Mobile phase A (0.1% formic acid in water); Mobile phase B (0.1% formic acid in acetonitrile); Flow rate: 0.1-0.6 μL/min (0.4 μL/min is preferred); Gradient: 0 min (3% B), 3 min (3% B), 5 min (95% B), 12 min (95% B), 12.1 min (3% B), 25 min (3% B).
4. Chip Cube Conditions: Injection Flushing Volume (2-4 μL)
(3) Mass Spectrometry (MS) Conditions:
Instruments: Agilent QQQ 6410A; Drying gas temperature: 325° C.; Drying gas flow:
4 L/min; Capillary voltage: 1950V; Polarity: Positive ion mode; Scan mode: Multiple
Reaction Monitoring (MRM)
The ion pair used in the method of the present invention for detecting some of these drugs in the urine samples includes:
   i. Ketamine: 238.1>128.0, 238.1>89.0;
   ii. Methadone: 310.2>265.1, 310.2>91.0;
   iii. Morphine: 286.1>128.1, 286.1>115.0;
   iv. 6-acetylmorphine (metabolite of heroin): 328.0>165.0, 328.0>211.0;
   v. Cocaine: 304.2>105.0, 304.2>182.1;
   vi. Benzoylecgonine (metabolite of cocaine): 290.1>168.0, 290.1>105;
   vii. Amphetamine: 136.1>91.0, 136.1>119.0;
   viii. Methamphetamine: 150.1>65.0, 150.1>91.0;
   ix. MDMA: 194.1>163.0, 194.1>105;
   x. MDA: 180.1>135.0, 180.1>163.0

Example 19

Detection of Drug Residues by HPLC-Chip-MS/MS Method in Oral Secretion of Drug Abuser (1) Sample Preparation:
Ethyl acetate was added to the oral secretion samples. Then the samples were treated with liquid-liquid extraction by ultrasonication for 2 mins. Layer of ethyl acetate was collected and concentrated. The concentrated samples were resuspended by 50 μL of acetonitrile for analysis.
(2) Liquid Chromatography Conditions and (3) Mass Spectrometry Conditions are the Same as Example 18.

Example 20

Detection of Drug Residues by HPLC-Chip-MS/MS Method in Sweat of Drug Abuser (1) Sample Preparation:
Filter paper was put under the armpit of the subject. Sweat was collected for 20 mins in a 35° C. temperature control room. The filter paper was then cut into small pieces. Dichloromethane was added and shake thoroughly. After brief centrifugation, the dichloromethane layer was collected and concentrated. The concentrated sample was resuspended by 50 μL of acetonitrile for analysis.
(2) Liquid Chromatography Conditions and (3) Mass Spectrometry Conditions are the Same as Example 18

If desired, the different functions discussed herein may be performed in a different order and/or concurrently with each other. Furthermore, if desired, one or more of the above-described functions may be optional or may be combined Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

INDUSTRIAL APPLICATION

The present invention can fulfill different demands of drug testing. The methods of the present invention only require lesser specimen amount but are highly specific and sensitive, low in cost, accurate and reliable. The present invention can be applied by government executive agency, inspection units and pharmaceutical industry.

What we claim:

1. A method for detecting drug residues as low as picogram level in human body by incorporating high performance liquid chromatography with chip and mass spectrometry (HPLC-Chip-MS/MS) for detecting drug residues in human hair, the method comprises:
    (1) Sample preparation;
    (2) Liquid chromatography; and
    (3) Mass spectrometry,
    wherein the (1) sample preparation further comprises:
    (i) collecting the human hair at different lengths from a human subject;
    (ii) washing the collected human hair in 0.2% SDS, deionized water and acetone by ultrasonication;
    (iii) drying the washed human hair by nitrogen gas followed by digesting the dried hair sample with 0.5 mL hydrochloric acid at a concentration of 0.15 mol/L for 4 hours at 60° C.;
    (iv) cooling the digested human hair to room temperature followed by neutralizing with 0.03 mL sodium hydroxide at a concentration of 2 mol/L and 2 mL sodium phosphate buffer at a concentration of 0.1 mol/L in pH 6.8;
    (v) adding 2 mL extraction mixture comprising 90:10 v/v, dichloromethane:hexane for phase extraction by vortexing for 5 minutes followed by centrifugation;
    (vii) collecting lower organic phase and drying the lower organic phase by nitrogen gas;
    (viii) resuspending the dried lower organic phase with 50 μL acetonitrile and the resuspension is ready for liquid chromatography, and
    wherein the (2) liquid chromatography further comprises:
    (i) A single chip being directly installed on an ion source with a micro-camera for monitoring of ionization spray from said ion source; and (ii) A capillary pump having the following conditions: Mobile phase A is 0.1-0.2% of formic acid in water; Mobile phase B is 0.1-0.2% formic acid in acetonitrile; a flow rate of 1-6 μL/min; Mobile phase A gradient is 10-97%; and Mobile phase B gradient is 90-3%; or (iii) A nano pump having the following conditions: Mobile phase A and B are the same to that of said capillary pump; Flow rate used is 0.1-0.6 μL/min; Mobile phase A gradient is 5-97%; Mobile phase B gradient is 95-3%; and (iv) A chip injection volume which is 2-4 μL, and wherein the (3) mass spectrometry further comprises:
  (i) a drying gas temperature of 325° C.;
  (ii) a drying gas flow of 4 L/min;
  (iii) a capillary voltage of 1950V;
  (iv) a polarity in positive ion mode;
  (v) a scan mode in Multiple Reaction Monitoring (MRM); and
  (vi) an ion pair for detection of product ions, and wherein the drug residues comprises one or more of ketamine, methadone, morphine, 6-acetylmorphine, cocaine, benzoylecgonine, amphetamine, methamphetamine, MDMA and MDA.

2. The method according to claim 1, wherein said ion pair for detecting product ions of ketamine is 238.1>128.0, 238.1>89.0.

3. The method according to claim 1, wherein said ion pair for detecting product ions of methadone is 310.2>265.1, 310.2>91.0.

4. The method according to claim 1, wherein said ion pair for detecting product ions of morphine and 6-acetylmorphine are 286.1>128.1, 286.1>115.0 and 328.0>165.0, 328.0>211.0, respectively.

5. The method according to claim 1, wherein said ion pair for detecting product ions of cocaine and benzoylecgonine are 304.2>105.0, 304.2>182.1 and 290.1>168.0, 290.1>105, respectively.

6. The method according to claim 1, wherein said ion pair for detecting product ions of amphetamine and methamphetamine are 136.1>91.0, 136.1>119.0 and 150.1>65.0, 150.1>91.0, respectively.

7. The method according to claim 1, wherein said ion pair for detecting product ions of MDMA and MDA are 194.1>163.0, 194.1>105 and 180.1>135.0, 180.1>163.0, respectively.

8. The method according to claim 1, wherein the limit of detection (LOD) and the limit of quantification (LOQ) for detecting ketamine are 0.1 pg/mg and 1 pg/mg respectively.

9. The method according to claim 1, wherein the limit of detection (LOD) and the limit of quantification (LOQ) for detecting methadone are 0.1 pg/mg and 0.5 pg/mg respectively.

10. The method according to claim 1, wherein the limit of detection (LOD) and the limit of quantification (LOQ) for detecting morphine and 6-acetylmorphine are 2 pg/mg and 10 pg/mg respectively.

11. The method according to claim 1, wherein the limit of detection (LOD) and the limit of quantification (LOQ) for detecting cocaine and benzoylecgonine are 0.1 pg/mg and 0.5 pg/mg respectively.

12. The method according to claim 1, wherein the limit of detection (LOD) and the limit of quantification (LOQ) for detecting amphetamine are 0.3 pg/mg and 1 pg/mg respectively.

13. The method according to claim 1, wherein the limit of detection (LOD) and the limit of quantification (LOQ) for detecting methamphetamine are 0.1 pg/mg and 0.5 pg/mg respectively.

14. The method according to claim 1, wherein the limit of detection (LOD) and the limit of quantification (LOQ) for detecting MDMA are 0.1 pg/mg and 0.1 pg/mg, respectively; the limit of detection (LOD) and the limit of quantification (LOQ) for detecting MDA are 0.5 pg/mg and 0.5 pg/mg, respectively.

15. A system of detecting drug residues in human body according to the method described in claim 1.

* * * * *